United States Patent [19]
Enari et al.

[11] Patent Number: 5,401,736
[45] Date of Patent: Mar. 28, 1995

[54] 4,5,6,7-TETRAHYDRO-1H-IMIDAZO[4,5-C]PYRIDINE-6-CARBOXYLIC ACID AMIDE

[75] Inventors: Hiroyuki Enari, Tokyo; Mikiro Yanaka, Matsudo, both of Japan

[73] Assignee: Kureha Kagaku Kogyo Kabushiki Kaisha, Tokyo, Japan

[21] Appl. No.: 121,493

[22] Filed: Sep. 16, 1993

[30] Foreign Application Priority Data

Sep. 22, 1992 [JP] Japan .................... 4-276688

[51] Int. Cl.$^6$ .................... A61K 31/435; C07D 471/04
[52] U.S. Cl. .................... 514/210; 514/228.5; 514/234.5; 514/253; 514/303; 546/118; 544/58.4; 544/127; 544/362
[58] Field of Search ............ 546/118; 544/58.4, 127, 544/362; 514/303, 228.5, 234.5, 253, 210

[56] References Cited

U.S. PATENT DOCUMENTS 5,091,390  2/1992  Ardecky et al. .................... 514/303

OTHER PUBLICATIONS

C. J. Blankley et al "Synthesis and structure–activity . . ." Journal of Medicinal Chemistry, vol. 34, 1991, Washington, US, pp. 3248–3260.

J. C. Hodges "Regiospecific synthesis of 3-substituted . . ." Synthesis, No. 1, 1987, Stuttgard De, pp. 20–24.

K. Barlos et al "Eine einfache synthese . . ." Liebigs Annalen Der Chemie, 1989, Weinheim DE, pp. 387–388.

R. J. Howard et al "Inhibitory effects of . . ." Chemical Abstracts, vol. 105, No. 23, 1986, Columbus, Ohio US, Abstract #205895d, p. 325. Abstract Only.

G. C. Stelakatos et al "On the trityl method for . . ." Journal of the American Chemical Society, vol. 81, 1959, Washington, D.C. pp. 2884–2887.

M. Del Mar Sanchez-Sanchez et al "The Pictet-Spengler reaction . . ." Chemical Abstracts, vol. 118, No. 19, 1993, Columbus, Ohio US, Abstract #192077e, 992. Abstr. Only.

Biorganic & Medicinalal Chemistry Letters, vol. 1, No. 12, pp. 711–716, 1991 Middlemiss et al "Bromobenzofurans: A new Class of Potent, Non–peptide etc".

Primary Examiner—Mukund J. Shah
Assistant Examiner—Matthew V. Grumbling
Attorney, Agent, or Firm—Nixon & Vanderhye

[57] ABSTRACT

Disclosed herein are 4,5,6,7-tetrahydro-1H-imidazo[4,5-c]pyridine-6-carboxylic acid amide derivatives having a high antagonistic activity against angiotensin II and a high specificity to angiotensin II receptors, intermediates for preparing the derivatives, and antagonists against angiotensin II comprising the derivatives.

7 Claims, No Drawings

4,5,6,7-TETRAHYDRO-1H-IMIDAZO[4,5-C]PYRIDINE-6-CARBOXYLIC ACID AMIDE

BACKGROUND OF THE INVENTION

The present invention relates to 4,5,6,7-tetrahydro-1H-imidazo[4,5-c]pyridine-6-carboxylic acid amide derivatives, intermediates for preparing the derivatives, and antagonists against angiotensin II (AII) comprising the derivatives.

Angiotensin II is an octapeptide hormone typically relating to hypertension, central nervous system diseases. It is therefore known that inhibition of the activities of angiotensin II is effective for the treatment of the hypertension and the central nervous system diseases.

As angiotensin II inhibitors, there have been developed a renin inhibitor and an angiotensin-converting enzyme (ACE) inhibitor which inhibit the synthesis of angiotensin II. These inhibitors, however, have the problems that they are incapable of inhibiting the activities of angiotensin produced by other types of enzymes than renin and ACE, and that they may exert adverse effects to the other metabolic systems.

Angiotensin II acts through interaction with a specific receptor present in a cell membrane, so that an angiotensin II receptor antagonist which is capable of inhibiting all of the actions of the generated angiotensin II at the level of interaction with the receptor and gives no influence to the other metabolic systems has been desired as an antagonistic agent which is more specific and has less side effects.

Some peptide analogs such as Saralasin have been reported as angiotensin II receptor antagonists, but they are unsatisfactory in their antagonistic activities and also the area of their applications is limited because of their lack of oral absorptivity.

Recently, non-peptidic angiotensin II receptor antagonists have been reported as the agents free of the said problems. Examples of these antagonists are DuP753, PD123177 (Bio-organic & Medical Chemistry Letters, 1(12), 711–716, 1991) and 4,5,6,7-tetrahydro-1H-imidazo[4,5c]pyridine-6-carboxylic acid derivatives disclosed in U.S. Pat. No. 5,091,390, which are represented by the following structural formulae (1), (2), and (3), respectively:

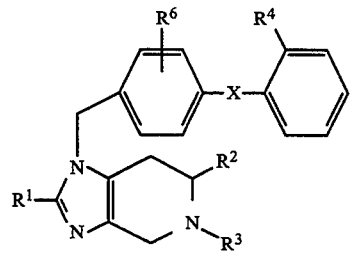
(1)

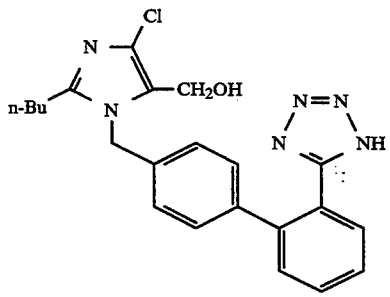
(2)

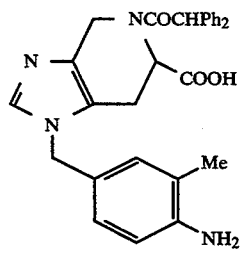

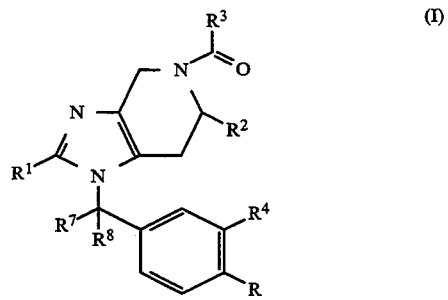
(3)

wherein for example, $R^1$ is hydrogen, $R^2$ is $CO_2H$, $R^3$ is $COCH(Ph)_2$, X is NHCO, $R^4$ is $CO_2H$, and $R^6$ is $CH_3$.

Nevertheless, request for the development of a compound having a higher specificity to the angiotensin II receptors and a higher antagonistic activity against angiotensin II is still rising.

In view of the above, the present inventors have extensive researches for wide range of compounds and, as a result, found that some specific 4,5,6,7-tetrahydro-1H-imidazo[4,5-c]pyridine-6-carboxylic acid amide derivatives have a noticeably high antagonistic activity against angiotensin II and a high specificity to angiotensin II receptors as compared with the known compounds. Based on this finding, the present invention has been attained.

SUMMARY OF THE INVENTION

In a first aspect of the present invention, there is provided a compound of the formula (I):

(I)

or a pharmaceutically acceptable salt thereof; wherein
$R^1$ represents
  hydrogen atom,
  halogen atom,
  $C_1$–$C_6$ alkyl,
  $C_3$–$C_6$ alkenyl,
  $C_3$–$C_6$ alkynyl,
  $R^{20}$ $(CH_2)_n$— wherein $R^{20}$ represents $C_3$–$C_8$ cycloalkyl, naphthyl, phenyl, or phenyl substituted with one to five of $C_1$–$C_4$ alkyl, halogen atom, trifluoromethyl, hydroxy, $C_1$–$C_4$ alkoxy, $C_1$–$C_3$ acyloxy, amino, N-mono-$C_1$–$C_4$ alkylamino, N-di-$C_1$–$C_4$ alkylamino, $C_1$–$C_4$ thioalkyl, $C_1$–$C_3$ alkylsulfonyl, nitro, and —$NHCOR^{21}$ wherein $R^{21}$ represents $C_1$–$C_3$ alkyl, phenyl, $C_1$–$C_3$ alkylphenyl, aminophenyl, or $C_1$–$C_4$ alkylaminophenyl, and n is an integer of 1 to 6,
  $R^{20}$—C(O)— wherein $R^{20}$ is as defined above, or
  $R^{20}$—CH(OH)— wherein $R^{20}$ is as defined above;
$R^2$ represents carbamoyl, mono- or di-$C_1$–$C_6$ alkylcarbamoyl, or 4- to 6-membered heterocyclic carbamoyl;

R represents amino, carboxy, (1H-tetrazol-5-yl)phenyl, carboxyphenyl, carboxybenzamido, (1H-tetrazol-5-yl)benzamido, carboxyphenylcarbamoyl, or (1H-tetrazol-5-yl)-phenylcarbamoyl;

$R^3$ represents —$CH_2$(phenyl), —CH(phenyl)$_2$, —CH(phenyl)$CH_3$, —CH(phenyl)(cyclohexyl), —$CH_2CH_2$(phenyl), —$CH_2$($C_1$-$C_6$ alkoxyphenyl), or —$CH_2$(hydroxyphenyl); and $R^4$, $R^7$, and $R^8$ each represent independently hydrogen atom or $C_1$-$C_6$ alkyl.

In a second aspect of the present invention, there are provided intermediates for producing the compound as defined in the first aspect of the present invention.

In a third aspect of the present invention, there is provided an angiotensin II antagonist comprising the compound as defined in the first aspect of the present invention.

DETAILED DESCRIPTION OF THE INVENTION

The compound of the formula (I) or the pharmaceutically acceptable salt thereof have a noticeably high antagonistic activity against angiotensin II and a high specificity to angiotensin II receptors.

Preferred is a compound of the formula (I) or a pharmaceutically acceptable salt thereof wherein $R^1$ is hydrogen atom or $C_1$-$C_6$ alkyl group; $R^2$ is —$CONH_2$, —$CONHCH_3$, —$CON(CH_3)_2$, —$CONH(C_2H_5)$, —$CON(C_2H_5)_2$,

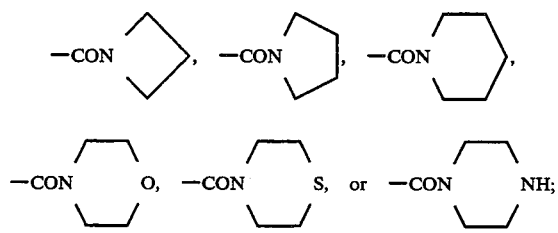

R is amino, carboxy, 2-(1H-tetrazol-5-yl)phenyl, 2-carboxyphenyl, 2-carboxybenzamido, 2-(1H-tetrazol-5-yl)benzamido, 2-carboxyphenylcarbamoyl, or 2-(1H-tetrazol-5-yl)phenylcarbamoyl; $R^3$ is —CH(phenyl)$_2$, —$CH_2$(phenyl), —CH(phenyl)$CH_3$, —CH(phenyl)(cyclohexyl), —$CH_2CH_2$(phenyl), —$CH_2$(p-methoxyphenyl), or —$CH_2$(p-hydroxyphenyl); and $R^4$, $R^7$, and $R^8$ each are independently hydrogen atom or $C_1$-$C_2$ alkyl.

The compound of the present invention has an asymmetric carbon atom at the 6-position of the condensed imidazole ring. Accordingly, the present invention includes any single stereoisomer thereof. Also, the present invention includes a mixture of stereoisomers. Preferably, the compound of the present invention is a stereoisomer in which the 6-position of the condensed imidazole ring is S configuration.

The pharmaceutically acceptable salt of the compound of the present invention can be obtained by using an acid or a base which is commonly employed in the field of pharmacy. Preferred examples of the acid include organic and inorganic acids such as hydrochloric acid, sulfuric acid, methanesulfonic acid, benzenesulfonic acid, and p-toluenesulfonic acid. Preferred examples of the organic base include mono-, di-, or trialkylamines such as methylamine, dimethylamine, and triethylamine, and mono-, di-, or trihydroxyalkylamines such as mono-, di-, or triethanolamine. Preferred examples of the inorganic base include hydroxides, carbonates, and bicarbonates of ammonium, sodium, lithium, potassium, calcium, magnesium, aluminum, zinc, and the like.

The term "halogen atom" used herein means an atom of fluorine, chlorine, bromine, and iodine.

In the present invention, the phenyl group having a substituent may have its substituent or substituents at any of the o-, m-, and p-positions unless otherwise specified.

An example of a process for preparing a compound of the present invention (hereinafter called process A) is shown in Scheme I.

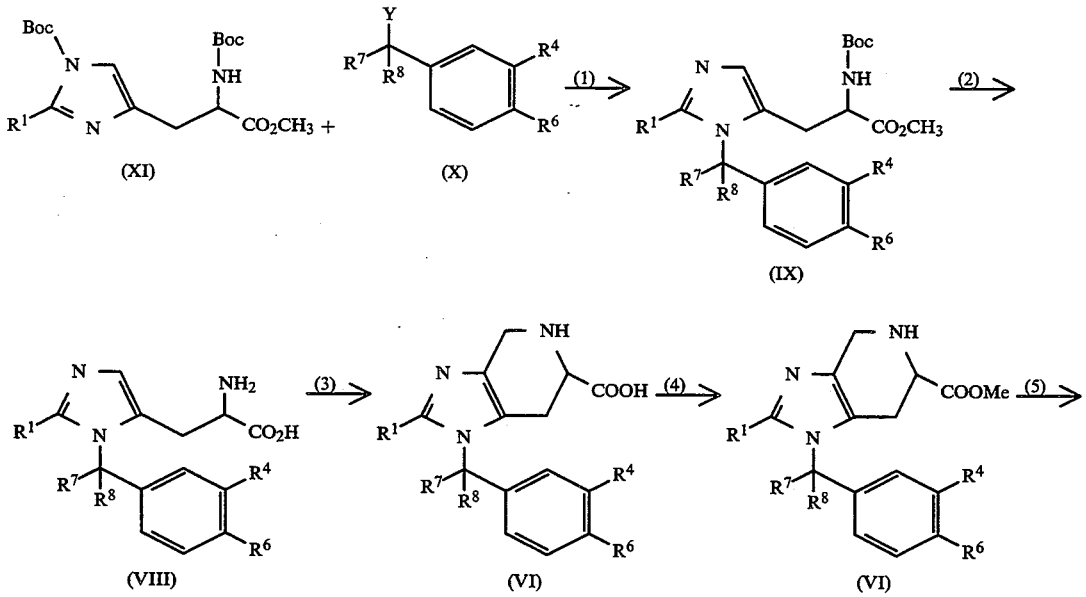

Scheme I

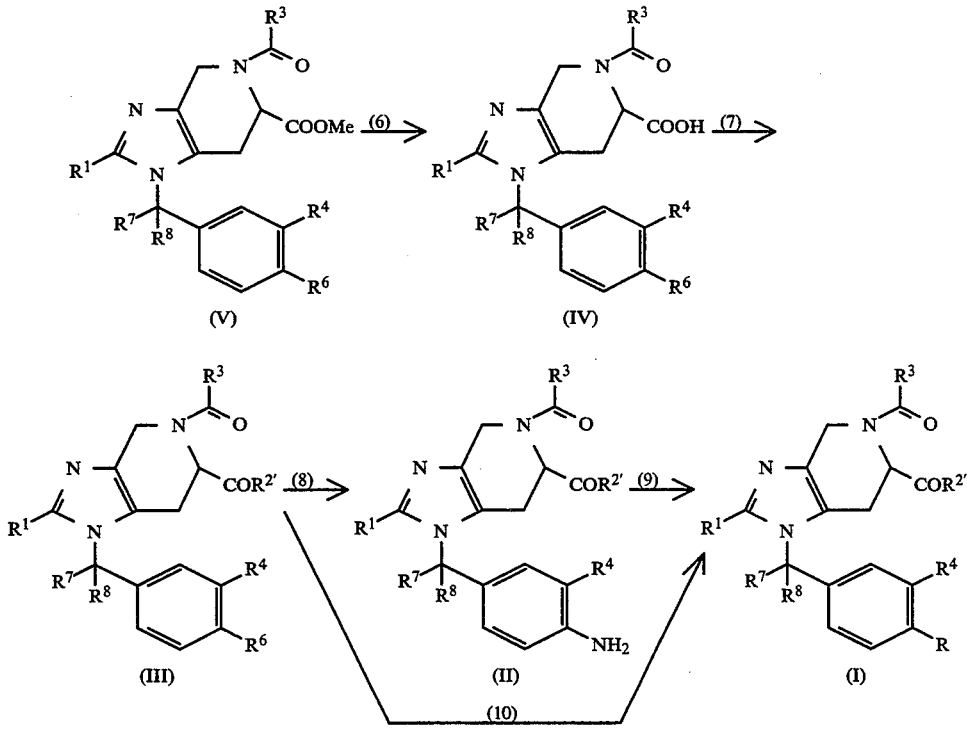

With reference to Scheme I, the process A is described by dividing the process into ten steps (1)-(10).

STEP (1)

A compound of the formula (XI) wherein $R^1$ is as defined above and Boc stands for tertiary butoxycarbonyl, is reacted with a compound of the formula (X) wherein Y is OH, Cl, Br, or $OSO_2CF_3$; $R^4$ is H or $C_1$-$C_6$ alkyl; $R^6$ is $NO_2$, cyanophenyl, cyano, (1H-tetrazol-5-yl) phenyl, or $C_1$-$C_3$ alkoxycarbonyl; and $R^7$ and $R^8$ each are independently H or $C_1$-$C_6$ alkyl, at 0° to 60° C. for 10 to 48 hours to obtain a compound of the formula (IX) wherein $R^1$, $R^4$, $R^6$, $R^7$, $R^8$, and Boc are as defined above.

STEP (2)

The compound of the formula (IX) obtained in the step (1) is treated with an acid, such as hydrochloric acid, to obtain a compound of the formula (VIII) wherein $R^1$, $R^4$, $R^6$, $R^7$, and $R^8$ are as defined above.

STEP (3)

To the compound of the formula (VIII), there are added an acid and HCHO, and the mixture is reacted at 10° to 150° C. for 0.5 to 4 hours to obtain a compound of the formula (VII) wherein $R^1$, $R^4$, $R^6$, $R^7$, and $R^8$ are as defined above.

STEP (4)

The compound of the formula (VII) is suspended in an alcohol/trimethyl orthoformate mixture and then HCl is blown into the suspension to carry out reaction at 60° to 100° C. for 4 to 8 hours to obtain a compound of the formula (VI) wherein $R^1$, $R^4$, $R^6$, $R^7$, and $R^8$ are as defined above.

STEP (5)

The compound of the formula (VI) is added to a solution of acetonitrile, chloroform, dimethylformamide, or THF containing carbodiimide, 1-hydroxybenztriazole, diphenylacetic acid, or phenylcyclohexylacetic acid and reacted at 10° to 40° C. for 10 to 48 hours to obtain a compound of the formula (V) wherein $R^1$, $R^4$, $R^6$, $R^7$, and $R^8$ are as defined above; and $R^3$ is —CH(phenyl)$_2$, —CH(phenyl)(cyclohexyl), —CH$_2$(-phenyl), —CH$_2$CH$_2$(phenyl), —CH(phenyl)CH$_3$, —CH$_2$($C_1$-$C_6$ alkoxyphenyl), or —CH$_2$(hydroxyphenyl).

STEP (6)

An alkali, e.g. NaOH, is added to the compound of the formula (V) to obtain a compound of the formula (IV) wherein $R^1$, $R^3$, $R^4$, $R^6$, $R^7$, and $R^8$ are as defined above

STEP (7)

A nitrogen-containing compound is added to the compound of the formula (IV) and the mixture is reacted at 10° to 40° C. for 10 to 24 hours to obtain a compound of the formula (III) wherein $R^1$, $R^3$, $R^4$, $R^6$, $R^7$, and $R^8$ are as defined above; and $R^{2'}$ is amino, mono- or di-$C_1$-$C_6$ alkylamino, or 4- to 6-membered heterocyclic amino.

When $R^6$ is (1H-tetrazol-5-yl)phenyl, it is obtained a compound of the formula (I) wherein R is (1H-tetrazol-5-yl)phenyl, in this step.

STEP (8)

Tin chloride dihydrate is added to the compound of the formula (III) wherein $R^6$ is $NO_2$ and the mixture is reacted at 40° to 100° C. for 10 to 120 minutes to obtain a compound of the formula (II) wherein $R^1$, $R^{2'}$, $R^3$, $R^4$, $R^7$, and $R^8$ are as defined above.

STEP (9)

A benzoic acid derivative is reacted with the compound of the formula (II) at 10° to 40° C. for 10 to 24 hours to obtain a compound of the formula (I) wherein $R^1$, $R^{2'}$, $R^3$, $R^4$, $R^7$, and $R^8$ are as defined above.

STEP (10)

When $R_6$ is cyanophenyl, there can be obtained a compound of the formula (I) wherein X is a C—C single bond, by hydrolyzing the compound of the formula (III).

A compound of the formula (XI) (raw material) can be obtained by the method described in J. Am. Chem. Soc., 114 (5), 1906–1908, 1992.

A compound of the formula (X) (raw material) can be obtained, for example, by the method described in J. Med. Chem., 33, 1312–1329, 1990, J. Med. Chem., 34, 2525–2547, 1991, J. Med. Chem., 34, 3248–3260, 1991, etc.

Conversion of substituents may be made by the conventional method available to one ordinarily skilled in the art.

Another example of a process for producing the compound of the present invention (hereinafter referred to as process B) is described in Scheme II.

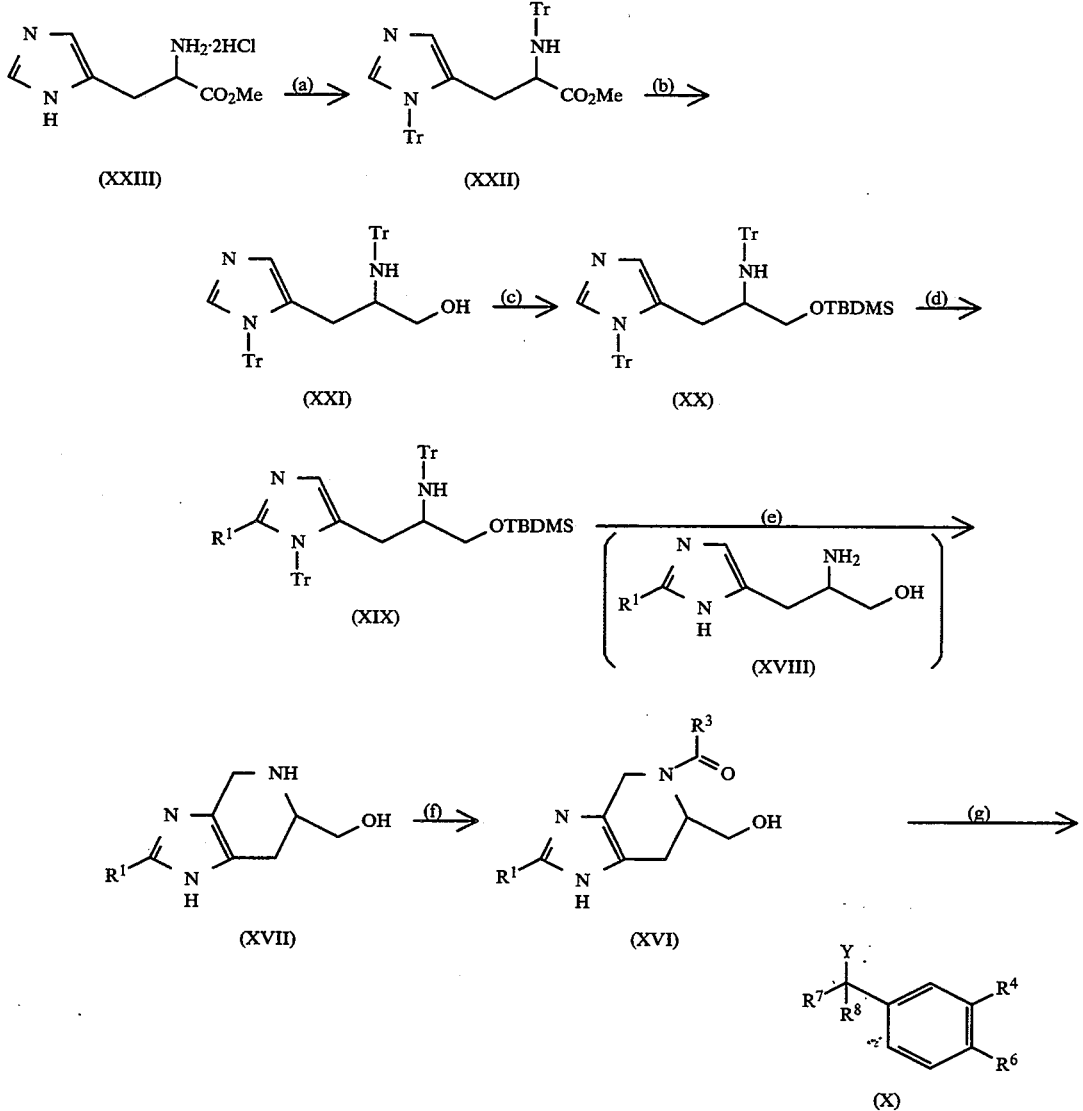

-continued
Scheme II
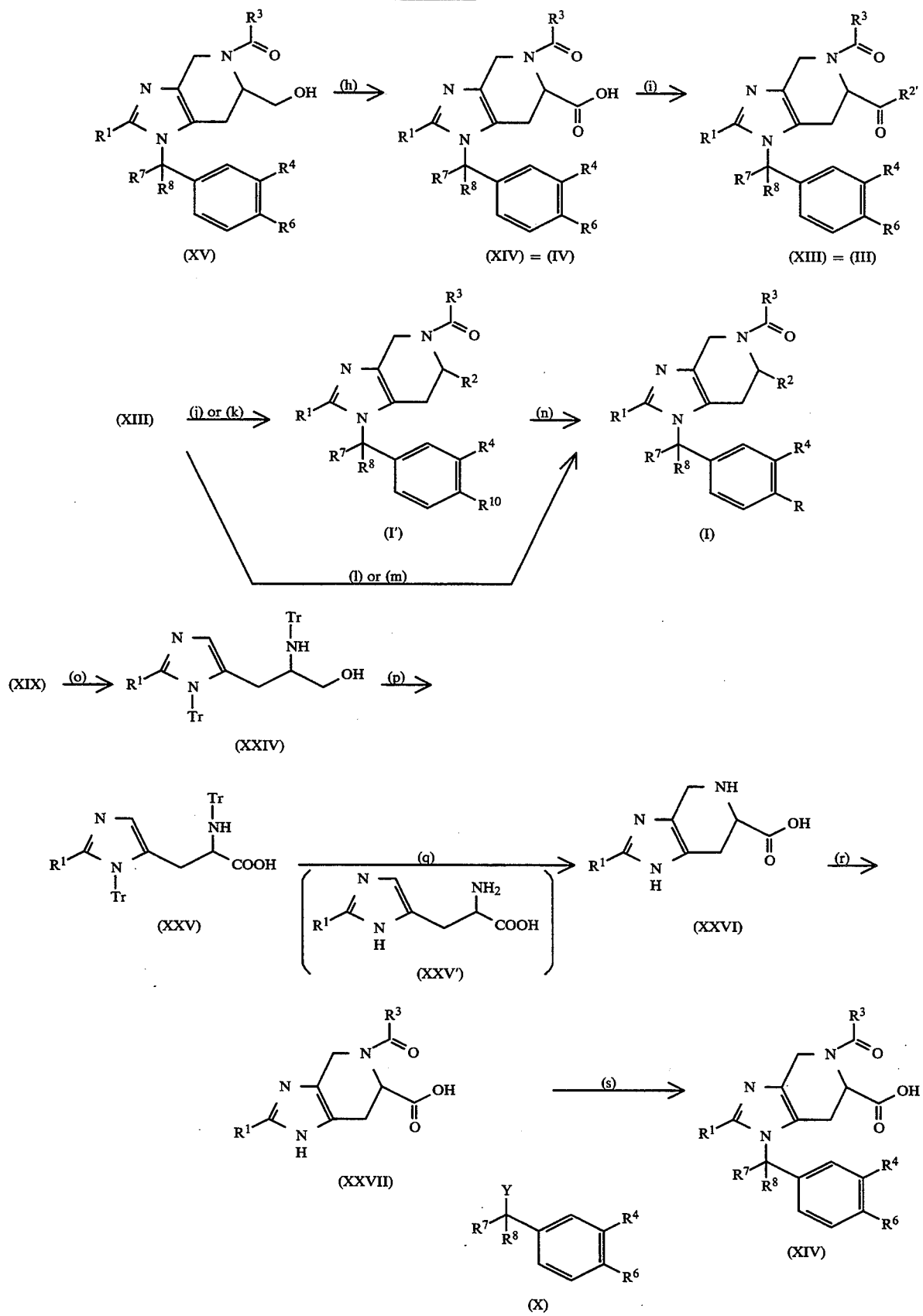

With reference to Scheme II the process B is described by dividing the process into 19 steps (a)–(s).

STEP (a)

A compound of the formula (XXIII) is reacted with a tertiary amine such as Tr (triphenylmethyl) chloride and triethylamine in a solvent such as ether, THF (tetrahydrofuran), dioxane, methylene chloride, and chloroform at 10° to 60° C. for 2 to 24 hours to obtain a compound of the formula (XXII). The compound of the formula (XXIII) is commercially available.

STEP (b)

The compound of the formula (XXII) is reacted with a reducing agent such as lithium aluminum hydride in a solvent such as ether, THF, and dioxane at 0° to 40° C. for 0.1 to 1 hour to obtain a compound of the formula (XXI).

STEP (c)

The compound of the formula (XXI) is reacted with TBDMS (tertiary butyldimethylsilyl) chloride and imidazole in a solvent such as DMF (dimethylformamide) at 0° to 40° C. for 0.5 to 6 hours to obtain a compound of the formula (xx).

STEP (d)

The compound of the formula (XX) is dissolved in a solvent such as ether, THF, and dioxane in an atmosphere of an inert gas such as nitrogen or argon gas, and reacted with a $R^1$ halide (chloride, bromide, or iodide) in the presence of a base such as butyl lithium (normal, secondary, or tertiary) and HMPA (hexamethylphosphoramide) at 0° to 40° C. for 0.1 to 6 hours to obtain a compound of the formula (XIX).

STEP (e)

An acid such as hydrochloric acid, is added to the compound of the formula (XIX) and the mixture is reacted at 10° to 120° C. for 0.5 to 6 hours to obtain a compound of the formula (XVIII). This compound may be isolated. When it is not isolated, an aqueous HCHO solution is directly added thereto, and the mixture is reacted at 10 to 120 for 0.5 to 6 hours to obtain a compound of the formula (XVII).

STEP (f)

The compound of the formula (XVII) is added to a solution of acetonitrile, chloroform, or THF containing carbodiimide, 1-hydroxybenztriazole, and $R^3COOH$, and reacted at 10° to 60° C. for 1 to 48 hours to obtain a compound of the formula (XVI).

STEP (g)

The compound of the formula (XVI) and a compound of the formula (X) are reacted in a solvent such as acetone, DMF, ether, THF, and chloroform in the presence of an appropriate base such as anhydrous potassium carbonate at 10° to 60° C. for 1 to 48 hours to obtain a compound of the formula (XV).

STEP (h)

The compound of the formula (XV) is reacted with an oxidizing agent such as chromic acid in a solvent such as acetone, methylene chloride, and chloroform at 10° to 40° C. for 0.1 to 3 hours to obtain a compound of the formula (XIV).

STEP (i)

The compound of the formula (XIV) is added to a solution of acetonitrile, chloroform, or THF containing carbodiimide, 1-hydroxybenztriazole, and linear or cyclic alkylamine, and reacted at 10° to 60° C. for 1 to 48 hours to obtain a compound of the formula (XIII).

STEP (j)

When $R^6$ is methoxycarbonyl, an alkali such as a sodium hydroxide is added to a solution of the compound of the formula (XIV) in an alcohol, ether, THF, or a mixture thereof, and reacted at 10° to 40° C. for 1 to 24 hours to obtain a compound of the formula (I') wherein $R^{10}$ is carboxy.

STEP (k)

When $R^6$ is nitro, tin chloride, or tin chloride dihydrate is added to a solution of the compound of the formula (XIII) in ethyl acetate, an alcohol, or a mixture thereof, and reacted in an atmosphere of an inert gas such as nitrogen or argon gas at 10° to 100° C. for 0.1 to 1 hour to obtain a compound of the formula (I') wherein $R^{10}$ is amino.

STEP (l)

When $R^6$ is cyanophenyl, trimethyltin azide or tributyltin azide is added to a solution of the compound of the formula (XIII) in toluene or xylene, and the mixture is reacted in an atmosphere of an inert gas such as nitrogen or argon gas at 100° to 120° C. for 12 to 120 hours, followed by a treatment with an acid such as hydrochloric acid to obtain a compound of the formula (I) wherein $R^{10}$ is 1H-tetrazol-5-yl) phenyl.

STEP (m)

When $R^6$ is ((1-triphenylmethyl) -1H-tetrazol-5-yl)phenyl, the compound of the formula (XIII) is dissolved in a solvent such as THF and dioxane, and an acid such as hydrochloric acid is added to the solution. Then, the mixture is reacted at 10° to 100° C. for 0.1 to 6 hours to obtain a compound of the formula (I) wherein $R^{10}$ is (1H-tetrazol-5-yl)phenyl.

STEP (n)

When $R^{10}$ is carboxy or amino, the compound of the formula (I') is dissolved in a solvent such as chloroform, acetonitrile, THF, and dioxane, and reacted by adding a compound having a required group at 10° to 60° C. for 1 to 24 hours to obtain a compound of the formula (I).

STEP (o)

The compound of the formula (XIX) is dissolved in a solvent such as THF and ether, and reacted with tetra-n-butylammonium fluoride at 0° to 40° C. for 0.5 to 6 hours to obtain a compound of the formula (XXIV).

STEP (p)

The compound of the formula (XXIV) is dissolved in DMF, and reacted with PDC (pyridinium dichromate) at 0° to 40° C. for 0.5 to 24 hours to obtain a compound of the formula (XXV).

STEP (q)

An acid such as hydrochloric acid is added to the compound of the formula (XXV) and the mixture is reacted at 10° to 120° C. for 0.5 to 6 hours to obtain a compound of the formula (XXV'). This compound (XXV') may be isolated. When it is not isolated, an HCHO solution is directly added thereto and the mixture is reacted at 10° to 120° C. for 0.5 to 6 hours to obtain a compound of the formula (XXVI).

STEP (r)

The compound of the formula (XXVI) is added to a solution of acetonitrile, chloroform, or THF containing carbodiimide, dimethylformamide, 1-hydroxybenztriazole, and $R^3COOH$, and reacted at 10° to 60° C. for 1 to 48 hours to obtain a compound of the formula (XXVII).

STEP (s)

The compound of the formula (XXVII) is reacted with a compound of the formula (X) in a solvent such as acetone, DMF, ether, THF, and chloroform in the presence of an appropriate base such as anhydrous potassium carbonate at 10° to 60° C. for 1 to 48 hours to obtain a compound of the formula (XIV).

The compound of the formula (X) can be obtained, for instance, by a method described in J. Med. Chem., 34, 2525–2547, 1991, J. Med. Chem., 35, 4027–4038, 1992, etc.

The present invention also provides the following intermediate compounds (A) to (E) for the preparation of the compound represented by the formula (I) of the present invention.

(A) A compound of the formula (III'):

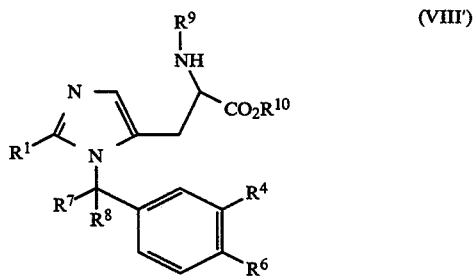

or a salt thereof; wherein
$R^1$ represents
  hydrogen atom,
  halogen atom,
  $C_1$-$C_6$ alkyl,
  $C_3$-$C_6$ alkenyl,
  $C_3$-$C_6$ alkynyl,
  $R^{20}(CH_2)_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —$NHCOR^{21}$ wherein $R^{21}$ represents $C_1$-$C_3$ alkyl, phenyl, $C_1$-$C_3$ alkylphenyl, aminophenyl, or $C_1$-$C_4$ alkylaminophenyl, and n is an integer of 1 to 6,
  $R^{20}$—C(O)— wherein $R^{20}$ is as defined above, or
  $R^{20}$—CH(OH)— wherein $R^{20}$ is as defined above;
$R^4$ is hydrogen atom or $C_1$-$C_6$ alkyl;
$R^6$ is nitro, (1-triphenylmethyl-1H-tetrazol-5-yl)phenyl, cyano, $C_1$-$C_3$ alkoxycarbonyl, or cyanophenyl;
$R^7$ and $R^8$ each are independently hydrogen atom or $C_1$-$C_6$ alkyl;
$R^9$ is hydrogen atom or t-butoxycarbonyl; and
$R^{10}$ is hydrogen atom or $C_1$-$C_6$ alkyl.

In the formula (XIII'), preferably $R^1$ is hydrogen atom or $C_1$-$C_6$ alkyl; $R^4$ is hydrogen atom or $C_1$-$C_2$ alkyl; $R^6$ is nitro, 2-(1-trifluoromethyl-1H-tetrazol-5-yl)phenyl, or 2-cyanophenyl; $R^7$ and $R^8$ each are independently hydrogen atom or $C_1$-$C_6$ alkyl; and $R^{10}$ is hydrogen atom or $C_1$-$C_6$ alkyl.

(B) A compound of the formula (XXVIII):

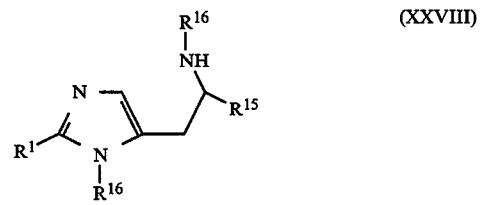

or a salt thereof; wherein
$R^1$ represents
  hydrogen atom,
  halogen atom,
  $C_1$-$C_6$ alkyl,
  $C_3$-$C_6$ alkenyl,
  $C_3$-$C_6$ alkynyl,
  $R^{20}(CH_2)_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —$NHCOR^{21}$ wherein $R^{21}$ represents $C_1$-$C_3$ alkyl, phenyl, $C_1$-$C_3$ alkylphenyl, aminophenyl, or $C_1$-$C_4$ alkylaminophenyl, and n is an integer of 1 to 6,
  $R^{20}$—C(O)— wherein $R^{20}$ is as defined above, or
  $R^{20}$—CH(OH)— wherein $R^{20}$ is as defined above;
$R^{15}$ represents —$CH_2$—$R^{17}$ wherein $R^{17}$ represents hydroxy or t-butyldimethylsilyloxy, or —C(O)—$R^{17}$ wherein $R^{17}$ is as defined above; and
$R^{16}$ represents hydrogen atom or triphenylmethyl; with proviso that when $R^1$ and $R^{16}$ are both hydrogen atom, $R^{15}$ is not —$CH_2$—OH, and that when $R^1$ is hydrogen atom or methyl and $R^{16}$ is hydrogen atom, $R^{15}$ is not —COOH.

(C) A compound of the formula (XXIX):

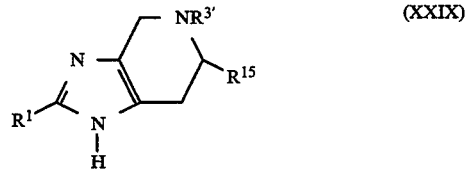

or a salt thereof; wherein
$R^1$ represents
  hydrogen atom,
  halogen atom,
  $C_1$-$C_6$ alkyl,
  $C_3$-$C_6$ alkenyl,
  $C_3$-$C_6$ alkynyl,
  $R^{20}(CH_2)_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —$NHCOR^{21}$ wherein $R^{21}$ represents $C_1$-$C_3$ alkyl, phenyl, $C_1$-$C_3$ alkylphenyl, aminophenyl, or $C_1$-$C_4$ alkylaminophenyl, and n is an integer of 1 to 6, $R^{20}$—C(O)— wherein $R^{20}$ is as defined above, or $R^{20}$—CH(OH)— wherein $R^{20}$ is as defined above;

$R^{15}$ represents —CH$_2$—$R^{17}$ wherein $R^{17}$ represents hydroxy or t-butyldimethylsilyloxy, or —C(O)—$R^{17}$ wherein $R^{17}$ is as defined above;

$R^3$ represents hydrogen atom, —COCH$_2$(phenyl), —COCH(phenyl)$_2$, —COCH(phenyl)CH$_3$, —COCH(phenyl)(cyclohexyl), —COCH$_2$CH$_2$(phenyl), —COCH$_2$($C_1$-$C_6$ alkoxyphenyl), or —COCH$_2$-(hydroxyphenyl);

with proviso that when $R^1$ and $R^{3'}$ are both hydrogen atom, $R^{15}$ is not —COOH.

In the formula (XXIX), preferably $R^1$ is hydrogen atom or $C_1$-$C_6$ alkyl; $R^{15}$ is —COOH; and $R^{3'}$ is —COCH(phenyl)$_2$ or —COCH(phenyl)(cyclohexyl).

(D) A compound of the formula (XXX):

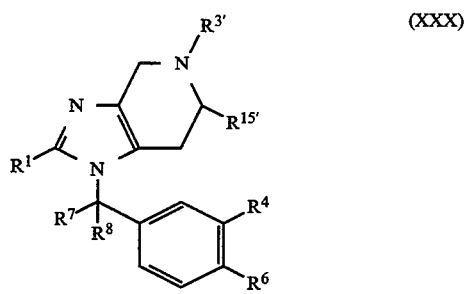

(XXX)

or a salt thereof; wherein
$R^1$ represents
hydrogen atom,
halogen atom,
$C_1$-$C_6$ alkyl,
$C_3$-$C_6$ alkenyl,
$C_3$-$C_6$ alkynyl, $R^{20}$(CH$_2$)$_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —NHCOR$^{21}$ wherein $R^{21}$ represents $C_1$-$C_3$ alkyl, phenyl, $C_1$-$C_3$ alkylphenyl, aminophenyl, or $C_1$-$C_4$ alkylaminophenyl, and n is an integer of 1 to 6, $R^{20}$—C(O)— wherein $R^{20}$ is as defined above, or $R^{20}$—CH(OH)— wherein $R^{20}$ is as defined above;

$R^{3'}$ represents hydrogen atom, —COCH$_2$(phenyl), —COCH(phenyl)$_2$, —COCH(phenyl)CH$_3$, —COCH(phenyl)(cyclohexyl), —COCH$_2$CH$_2$(phenyl), —COCH$_2$($C_1$-$C_6$ alkoxyphenyl), or —COCH$_2$-(hydroxyphenyl);

$R^4$, $R^7$, and $R^8$ each represent independently hydrogen atom or $C_1$-$C_6$ alkyl;

$R^6$ represents nitro, (1-triphenylmethyl-1H-tetrazol-5-yl)phenyl, cyano, $C_1$-$C_3$ alkoxycarbonyl, or cyanophenyl; and $R^{15}$ represents —CH$_2$—$R^{19}$ wherein $R^{19}$ represents hydrogen atom or $C_1$-$C_6$ alkyl group, or —C(O)—$R^{19}$ wherein $R^{19}$ is as defined above.

In the formula (XXX), preferably $R^1$ is hydrogen atom or $C_1$-$C_6$ alkyl; $R^{3'}$ is —COCH(phenyl)$_2$ or —COCH(phenyl)(cyclohexyl); $R^6$ is nitro, 2-(1-triphenylmethyl-1H-tetrazol-5-yl)phenyl, cyano, methoxycarbonyl, or 2-cyanophenyl; $R^4$, $R^7$, and $R^8$ each are independently hydrogen atom or $C_1$-$C_2$ alkyl; and $R^{19}$ is hydrogen atom or $C_1$-$C_2$ alkyl.

(E) A compound of the formula (XIII):

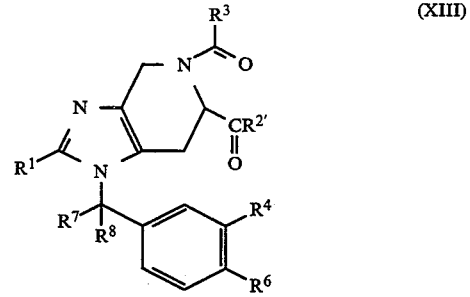

(XIII)

or a salt thereof; wherein
$R^1$ represents
hydrogen atom,
halogen atom,
$C_1$-$C_6$ alkyl,
$C_3$-$C_6$ alkenyl,
$C_3$-$C_6$ alkynyl, $R^{20}$(CH$_2$)$_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —NHCOR$^{21}$ wherein $R^{21}$ represents $C_1$-$C_3$ alkyl, phenyl, $C_1$-$C_3$ alkylphenyl, aminophenyl, or $C_1$-$C_4$ alkylaminophenyl, and n is an integer of 1 to 6, $R^{20}$—C(O)— wherein $R^{20}$ is as defined above, or $R^{20}$—CH(OH)— wherein $R^{20}$ is as defined above;

$R^{2'}$ represents amino, mono or di-$C_1$-$C_6$ alkylamino, or 4- to 6-membered heterocyclic amino;

$R^3$ represents —CH$_2$(phenyl), —CH(phenyl)$_2$, —CH(phenyl)CH$_3$, —CH(phenyl)(cyclohexyl), —CH$_2$CH$_2$(phenyl), —CH$_2$($C_1$-$C_6$ alkoxyphenyl), or —CH$_2$(hydroxyphenyl);

$R^4$, $R^7$ and $R^8$ each represent independently hydrogen atom or $C_1$-$C_6$ alkyl; and $R^6$ represents nitro, (1-triphenylmethyl-1H-tetrazol-5-yl)phenyl, $C_1$-$C_3$ alkoxycarbonyl, cyano, or 2-cyanophenyl.

In the formula (XIII), preferably $R^1$ is hydrogen atom or $C_1$-$C_6$ alkyl; $R^2$ is —NH$_2$, —NHCH$_3$, —N(CH$_3$)$_2$, —NH(C$_2$H$_5$), N(C$_2$H$_5$)$_2$,

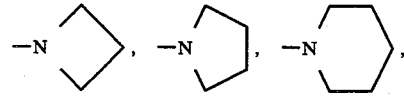

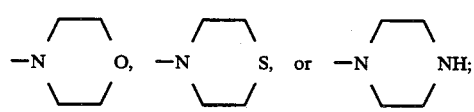

$R^3$ is —CH(phenyl)$_2$, or —CH(phenyl)(cyclohexyl); $R^4$, $R^7$, and $R^8$ each are independently hydrogen atom or $C_1$-$C_2$ alkyl; and $R^6$ is nitro, 2-(1-triphenylmethyl-1H-tetrazol-5-yl)phenyl, methoxycarbonyl, cyano, or 2-cyanophenyl.

The intermediate compounds of the present invention each have an asymmetric carbon atom at the 6-position of the condensed imidazole ring or the corresponding position. These intermediate compounds, therefore, include the single stereoisomer thereof. Also, the present invention includes a mixture of stereoisomers. In the present invention, these intermediate compounds are preferably the stereoisomers in which the 6-position of the condensed imidazole ring or the corresponding position is S configuration.

The salts of the above intermediate compounds can be obtained by using an acid or a base which is capable of chemically forming a salt with the intermediate compounds.

The formula (XIII') of (A) includes the formulae (IX) and (VIII) in the process A described above, and the formula (XXVIII) of (B) includes the formulae (XVIII), (XIX), (XXIV), (XXV), and (XXIII) in the process B described above. Also, the formula (XXIX) of (C) includes the formulae (XVII), (XVI), (XXVI), and (XXVII) in the process B, and the formula (XXX) of (D) includes the formulae (VII), (VI), (V), and (IV) in the process B. Therefore, these intermediate compounds (A) to (E) can be produced according to the process A or B.

The present invention further provides an angiotensin II antagonist comprising a compound of the formula (I) or a pharmaceutically acceptable salt thereof.

The compound of the present invention produces its pharmacological effect by competing with the receptor of angiotensin II and thereby inhibiting or suppressing the action of angiotensin II.

Particularly, the compound competes specifically with the $AT_1$ receptor (when $R^1$ in the formula (I) is not hydrogen atom) and the $AT_2$ receptor (when $R^1$ is hydrogen atom), which are known as angiotensin II receptors, according to the difference of $R^1$ in the formula (I). Also, as apparent from the Examples described later, the compound has a notably high antagonistic activity as compared with the known compounds.

Thus, the compound of the present invention is useful as a therapeutic agent for the diseases of the cardiovascular system and the central nervous system such as hypertension, heart diseases (cardiac hypertrophy, heart failure, myocardial infarction, et.), cerebral apoplexy, etc. The compound is also useful as a reagent or an agent for the studies on the role of angiotensin and its receptors.

When a substance of the present invention was given orally to the mice at a dosage of 300 mg/kg and they were observed for one week, none of the mice died in this period. This confirms that the compound of the present invention has no acute toxicity.

EXAMPLES

In the following, the present invention will be described with reference to the examples thereof. It is to be understood, however, that these examples are merely intended to be illustrative and not to be construed as limiting the scope of the invention.

Abbreviations used herein are as follows: cyc, cyclic; c-Hex, cyclohexyl; Ph, phenyl; Me, methyl; Et, ethyl; iPr, i-propyl; nPr, n-propyl; nBu, n-butyl; nHex, n-hexyl; Tr, triphenylmethyl.

EXAMPLE 1

Process A, Step (1)

Synthesis of 3-(3-methyl-4-nitrophenyl)methyl-N-t-butoxycarbonyl-L-histidine methyl ester (IX-2)

Trifluoromethanesulfonic anhydride (10.00 g, 0.0354 mol) and dry methylene chloride (60 ml) were placed into a 500 ml separable flask having its interior atmosphere replaced with well dried nitrogen gas, and cooled to −70° C. Then a solution of 3-methyl-4-nitrobenzyl alcohol (5.34 g, 0.0325 mol) and N,N-diisopropylethylamine (6.2 ml, 0.0356 mol) in dry methylene chloride (40 ml) was added dropwise over a period of 15 minutes, followed by stirring for 30 minutes, after which a solution of N,1-bis-t-butoxycarbonyl-L-histidine methyl ester (XI-2) (10.00 g, 0.0271 mol) in dry methylene chloride (40 ml) was further added dropwise over a period of 20 minutes. Thereafter, the reaction flask was taken out of the cooling bath and the mixture was stirred at room temperature for 6 hours. The reaction mixture during rapid stirring was poured into a 0.2M phosphate buffer solution (about 400 ml) to separate the methylene chloride layer, and the residue was washed with a 0.2M phosphate buffer solution (about 400 ml), dried over anhydrous sodium sulfate, filtered, and concentrated under reduced pressure to obtain an orange-colored oily material (12.07 g). This crude oily material was purified by silica gel column chromatography (LiChroprep Si60, 300 g, chloroform/methanol=30/1) to obtain the objective compound (IX-2) (4.45 g; yield: 39.3%) as a light-yellow oily material.

There were similarly synthesized the corresponding compounds by using the raw compounds of the formulae (XI) and (X) wherein $R^1$ was H, Et, iPr, nBu, or nHex, and $R^4$, $R^6$, $R^7$, $R^8$, and Y were as shown in Table 1 below.

TABLE 1

| Compound No. | $R^4$ | $R^6$ | $R^7$ | $R^8$ | Y |
|---|---|---|---|---|---|
| X-1 | H | $NO_2$ | H | H | OH |
| X-2 | Me | $NO_2$ | H | H | OH |
| X-3 | H | 2-CN-Ph | H | H | OH |
| X-4 | H | 2-CN-Ph | H | H | Br |
| X-5 | Me | 2-CN-Ph | H | H | Br |
| X-6 | H | 2-CN-Ph | H | H | $OSO_2CF_3$ |
| X-7 | Me | $NO_2$ | Me | Me | OH |
| X-8 | Me | 2-CN-Ph | Me | Me | Br |

EXAMPLE 2

Process A, Step (2)

Synthesis of 3-(3-methyl-4-nitrophenyl)methyl-L-histidine dihydrochloride (VIII-2)

A 6N hydrochloric acid solution (54.5 ml) was added to 3-(3-methyl-4-nitrophenyl)methyl-N-t-butoxycarbonyl-L-histidine methyl ester (IX-2) (1.3626 g, 0.00326 mol), and the mixture was refluxed under heating on a 120° C. oil bath for 2.5 hours. The resulting solution was cooled and then concentrated to obtain the objective compound (VIII-2) (1.1406 g; yield: 92.9%) as a light-brown oily material.

EXAMPLE 3

Process A, Step (3)

Synthesis of (S)-1-(3-methyl-4-nitrophenyl)methyl-4,5,6,7-tetrahydro-1H-imidazo[4,5-c]pyridine-6-carboxylic acid dihydrochloride (VII-2)

A 1N hydrochloric acid solution (13.7 ml) and a 37% formaldehyde solution (0.74 ml, 0.00907 mol) were added to 3-(3-methyl-4-nitrophenyl)methyl-L-histidine dihydrochloride (VIII-2) (1.1406 g, 0.00302 mol), and the mixture was stirred first at room temperature for half an hour and then on a 120° C. oil bath for 1.5 hours. The mixture was then cooled and concentrated to obtain the objective compound (VII-2) (1.1538 g; yield: 98.0%) as yellowish brown crystals (decomposed at 256.5°–258° C).

EXAMPLE 4

Process A, Step (4)

Synthesis of (S)-1-(3-methyl-4-nitrophenyl)methyl-4,5,6,7-tetrahydro-1H-imidazo[4,5-c]pyridine-6-carboxylic acid methyl ester (VI-2)

(S)-1-(3-methyl-4-nitrophenyl)methyl-4,5,6,7-tetrahydro-1H-imidazo[4,5-c]pyridine-6-carboxylic acid dihydrochloride (VII-2) (1.1538g, 0.00296 mol) was suspended in dry methanol (46 ml) and trimethylorthoformate (4.6 ml). Hydrogen chloride was blown into the suspension to saturation under ice cooling and stirring. The reaction solution was then stirred on a 90° C. oil bath for 6 hours, cooled, and concentrated. The resulting yellowish brown oily material (0.7456 g) was purified by silica gel column chromatography (Kiesegel 60, 60 g, chloroform/methanol= 15/1) to obtain the objective compound (VI-2) (0.7076 g; yield: 72.3%) as an orange oily material.

Similarly to Examples 1–4, there were synthesized the compounds of Table 2.

TABLE 2

| Compound No. | $R^1$ | $R^4$ | $R^6$ | $R^7$ | $R^8$ |
|---|---|---|---|---|---|
| VI-1 | H | H | $NO_2$ | H | H |
| VI-2 | H | Me | $NO_2$ | H | H |
| VI-3 | Et | Me | $NO_2$ | H | H |
| VI-4 | iPr | Me | $NO_2$ | H | H |
| VI-5 | nBu | Me | $NO_2$ | H | H |
| VI-6 | nHex | Me | $NO_2$ | H | H |
| VI-7 | H | H | 2-CN-Ph | H | H |
| VI-8 | nBu | H | 2-CN-Ph | H | H |
| VI-9 | nBu | Me | 2-CN-Ph | H | H |
| VI-10 | nBu | Me | $NO_2$ | Me | Me |
| VI-11 | nBu | Me | 2-CN-Ph | Me | Me |

EXAMPLE 5

Process A, Step (5)

Synthesis of (S)-5-diphenylacetyl-1-(3-methyl-4-nitrophenyl)methyl-4,5,6,7-tetrahydro-1H-imidazo[4,5-c]pyridine-6-carboxylic acid methyl ester (V-2)

Acetonitrile (16 ml) was added to a mixture of N,N'-dicyclohexylcarbodiimide (DCCI) (2.1080 g, 0.01022 mol), 1-hydroxybenzotriazole (HBTA) (1.3806 g, 0.01022 mol), and diphenylacetic acid (2.1685 g, 0.01022 mol), followed by stirring at room temperature for 20 minutes. A solution of (S)-1-(3-methyl-4-nitrophenyl)methyl-4,5,6,7-tetrahydro-1H-imidazo[4,5-c]pyridine-6-carboxylic acid methyl ester (VI-2) (2.7000 g, 0.00817 mol) in acetonitrile (14 ml) was added to the suspension, and the mixture was stirred at room temperature for 21 hours. An insoluble portion in the reaction mixture was filtered out and washed with acetonitrile, and then the filtrate and washings were joined and concentrated. The residue was dissolved in methylene chloride (40 ml), washed with a 10% sodium carbonate solution and a saturated brine, then dried over sodium sulfate and concentrated to obtain an orange oily material (4.5203 g). This crude oily material was purified by silica gel column chromatography (Kieselgel 60, 270 g, chloroform/methanol=60/11) to obtain the objective compound (V-2) (2.8250 g; yield: 65.9%) as colorless crystals (top: 174.5°–177° C.).

EXAMPLE 6

Process A, Step (6)

Synthesis of (S)-5-diphenylacetyl-1-(3-methyl-4-nitrophenyl)methyl-4,5,6,7-tetrahydro-1H-imidazo[4,5-c]pyridine-6-carboxylic acid (IV-2)

A 1N sodium hydroxide solution (5.7 ml) was added to a solution of (S)-5-diphenylacetyl-1-(3-methyl-4-nitrophenyl)methyl-4,5,6,7-tetrahydro-1H-imidazo[4,5c]pyridine-6-carboxylic acid methyl ester (V-2) (2.8250 g, 0.00539 mol) in tetrahydrofuran/methanol (3/1, 17 ml), and the mixture was left at room temperature for 6 hours. The reaction mixture was concentrated, and the residue was weakly acidified by adding a 1N hydrochloric acid solution (6.0 ml) and then extracted with methylene chloride. The methylene chloride layer was washed with a saturated brine, dried over anhydrous sodium sulfate, filtered, and concentrated under reduced pressure to obtain the objective compound (IV-2) (2.5558 g; yield: 93.0%) as a light-yellow viscous oily material. MS (EI) 492 (M-18).

The compounds of Table 3 were synthesized in the similar way to Examples 5 and 6.

TABLE 3

| Compound No. | $R^1$ | $R^3$ | $R^4$ | $R^6$ | $R^7$ | $R^8$ |
|---|---|---|---|---|---|---|
| IV-1 | H | $CH(Ph)_2$ | H | $NO_2$ | H | H |
| IV-2 | H | $CH(Ph)_2$ | Me | $NO_2$ | H | H |
| IV-3 | H | $CH(Ph)(cycC_6H_{11})$ | Me | $NO_2$ | H | H |
| IV-4 | Et | $CH(Ph)_2$ | Me | $NO_2$ | H | H |
| IV-5 | iPr | $CH(Ph)_2$ | Me | $NO_2$ | H | H |
| IV-6 | nBu | $CH(Ph)_2$ | Me | $NO_2$ | H | H |
| IV-7 | nhex | $CH(Ph)_2$ | Me | $NO_2$ | H | H |
| IV-8 | H | $CH(Ph)_2$ | H | 2-CN-Ph | H | H |
| IV-9 | nBu | $CH(Ph)_2$ | H | 2-CN-Ph | H | H |
| IV-10 | nBu | $CH(Ph)_2$ | Me | 2-CN-Ph | H | H |
| IV-11 | nBu | $CH(Ph)_2$ | Me | $NO_2$ | Me | Me |

TABLE 3-continued

| Compound No. | R¹ | R³ | R⁴ | R⁶ | R⁷ | R⁸ |
|---|---|---|---|---|---|---|
| IV-12 | nBu | CH(Ph)₂ | Me | 2-CN-Ph | Me | Me |

EXAMPLE 7

Process A, Step (7)

Synthesis of
(S)-N,N-dimethyl-5-diphenylacetyl-1-(3-methyl-4-nitrophenyl)methyl-4,5,6,7-tetrahydro-1H-imidazo[[4,5-c]pyridine-6-carboxamide (III-2)

Acetonitrile (40 ml) was added to a mixture of (S)-5-diphenylacetyl-1-(3-methyl-4-nitrophenyl) methyl-4,5,6,7-tetrahydro-1H-imidazo[4,5-c]pyridine-6-carboxylic acid (IV-2) (2.5558 g, 0.00501 mol), DCCI (1.2916 g, 0.00626 mol) and HBTA (0.8456 g, 0.00626 mol), and the mixture was stirred at room temperature for 20 minutes. Dimethylamine hydrochloride (0.4488 g, 0.00626 mol) was added to the resulting suspension, and the mixture was stirred at room temperature for 18 hours. An insoluble portion in the reaction solution was filtered out and washed with acetonitrile. The filtrate and washings were joined and concentrated. The residue was dissolved in chloroform (40 ml), washed with a 10% sodium carbonate solution and a saturated brine, then dried over sodium sulfate, and concentrated to obtain a light-yellow oily material (4.3025 g). This crude oily material was purified by silica gel column chromatography (Kieselgel 60, 220 g, chloroform/methanol=60/1) to obtain the objective compound (III-2) (2.3636 g; yield: 87.8%) as a light-yellow viscous oily material. MS (EI): 538 (M+1).

There were similarly synthesized the compounds of Table 4.

TABLE 4

| Compound No. | R¹ | R²' | R³ | R⁴ | R⁶ | R⁷ | R⁸ |
|---|---|---|---|---|---|---|---|
| III-1 | H | NMe₂ | CH(Ph)₂ | H | NO₂ | H | H |
| III-2 | H | NMe₂ | CH(Ph)₂ | Me | NO₂ | H | H |
| III-3 | H | NEt₂ | CH(Ph)₂ | Me | NO₂ | H | H |
| III-4 | H | NMe₂ | CH(Ph)(cyc C₆H₁₁) | Me | NO₂ | H | H |
| III-5 | H | cycNC₄H₈ | CH(Ph)₂ | Me | NO₂ | H | H |
| III-6 | H | cycNC₅H₁₀ | CH(Ph)₂ | Me | NO₂ | H | H |
| III-7 | H | cycNC₄H₈O | CH(Ph)₂ | Me | NO₂ | H | H |
| III-8 | H | NH2 | CH(Ph)₂ | H | NO₂ | H | H |
| III-9 | H | NHME | CH(Ph)₂ | H | NO₂ | H | H |
| III-10 | Et | NMe₂ | CH(Ph)₂ | Me | NO₂ | H | H |
| III-11 | iPr | NMe₂ | CH(Ph)₂ | Me | NO₂ | H | H |
| III-12 | nBu | NMe₂ | CH(Ph)₂ | Me | NO₂ | H | H |
| III-13 | nhex | NMe₂ | CH(Ph)₂ | Me | NO₂ | H | H |
| III-14 | H | NMe₂ | CH(Ph)₂ | H | 2-CN-Ph | H | H |
| III-15 | nBu | NMe₂ | CH(Ph)₂ | H | 2-CN-Ph | H | H |
| III-16 | nBu | NMe₂ | CH(Ph)₂ | Me | 2-CN-Ph | H | H |
| III-17 | nBu | NMe₂ | CH(Ph)₂ | Me | NO₂ | Me | Me |
| III-18 | nBu | NMe₂ | CH(Ph)₂ | Me | 2-CN-Ph | Me | Me |

EXAMPLE 8

Process A, Step (8)

Synthesis of
(S)-1-(4-amino-3-methylphenyl)methyl-N,N-dimethyl-5-diphenylacetyl-4,5,6,7-tetrahydro-1H-imidazo[4,5-c]pyridine-6-carboxamide (II-2)

(S)-N,N-dimethyl-5-diphenylacetyl-1-(3-methyl-4-nitrophenyl)methyl-4,5,6,7-tetrahydro-1H-imidazo[4,5-c]pyridine-6-carboxamide (III-2) (2.3636 g, 0.00440 mol) was dissolved in a mixture of 28 ml of ethyl acetate and 5 ml of methanol, followed by addition of tin chloride dihydrate (4.9580 g, 0.0220 mol) and agitation of the solution on an 80° C. oil bath in a stream of nitrogen for 30 minutes. The reaction mixture was cooled, neutralized by adding a 5% sodium carbonate solution, and concentrated. The residue was extracted with chloroform. The chloroform layer was washed with water, dried over sodium sulfate, and then concentrated to obtain a light-yellow foamy material (2.2368 g). This material was purified by silica gel column chromatography (Kieselgel 60, 120 g, chloroform methanol=50/1) to obtain the objective compound (II-2) (2.0077 g; yield: 90.0%) as a white foamy material. MS (EI): 508 (M+1).

There were similarly synthesized the compounds of Table 5.

TABLE 5

| Compound No. | R¹ | R²' | R³ | R⁴ | R⁷ | R⁸ |
|---|---|---|---|---|---|---|
| II-1 | H | NMe₂ | CH(Ph)₂ | H | H | H |
| II-2 | H | NMe₂ | CH(Ph)₂ | Me | H | H |
| II-3 | H | NEt₂ | CH(Ph)₂ | Me | H | H |
| II-4 | H | NMe₂ | CH(Ph)(cyc C₆H₁₁) | Me | H | H |
| II-5 | H | cycNC₄H₈ | CH(Ph)₂ | Me | H | H |
| II-6 | H | cycNC₅H₁₀ | CH(Ph)₂ | Me | H | H |
| II-7 | H | cycNC₄H₈O | CH(Ph)₂ | Me | H | H |
| II-8 | H | NH₂ | CH(Ph)₂ | H | H | H |
| II-9 | H | NHMe | CH(Ph)₂ | H | H | H |
| II-10 | Et | NMe₂ | CH(Ph)₂ | Me | H | H |
| II-11 | iPr | NMe₂ | CH(Ph)₂ | Me | H | H |
| II-12 | nBu | NMe₂ | CH(Ph)₂ | Me | H | H |
| II-13 | nhex | NMe₂ | CH(Ph)₂ | Me | H | H |
| II-14 | nBu | NMe₂ | CH(Ph)₂ | Me | Me | Me |

EXAMPLE 9

Process A, Step (9)

Synthesis of (S)-1-(4-(2-carboxybenzoylamino)-3-methylphenyl)-methyl-N,N-dimethyl-5-diphenylacetyl-4,5,6,7-tetrahydro-1H-imidazo[4,5-c]pyridine-6-carboxamide (I-2)

A solution of phthalic acid (0.7223 g, 0.00435 mol) in ethyl acetate (10 ml) was added to a solution of (S)-1-(4-amino-3-methylphenyl)methyl-N,N-dimethyl-5-diphenylacetyl-4,5,6,7-tetrahydro-1H-imidazo-[4,5-c]pyridine-6-carboxamide (II-2) (2.0077 g, 0.00396 mol) in ethyl acetate (30 ml) with stirring at room temperature. The mixture was stirred at room temperature for 23 hours, followed by filtration of the reaction mixture. The resulting white solid was washed with ethyl acetate (about 20 ml) and dried to obtain the objective compound (I-2, Compound No. 2) (2.4107 g; yield: 93.0%). MS 637 (EI): (M-18).

There were similarly synthesized the compounds of Table 6.

TABLE 6

| Compound No. | $R^1$ | $R^{2'}$ | $R^3$ | $R^4$ | R | $R^7$ | $R^8$ | MS(EI) |
|---|---|---|---|---|---|---|---|---|
| I-1 | H | NMe$_2$ | CH(Ph)$_2$ | H | 2-carboxybenzamido | H | H | 623(M-18) |
| I-2 | H | NM 2 | CH(Ph)$_2$ | Me | 2-carboxybenzamido | H | H | 637(M-18) |
| I-3 | H | NEt$_2$ | CH(Ph)$_2$ | Me | 2-carboxybenzamido | H | H | 665(M-18) |
| I-4 | H | NMe$_2$ | CH(Ph)(cyc C$_6$H$_{11}$) | Me | 2-carboxybenzamido | H | H | 643(M-18) |
| I-5 | H | cycNC$_4$H$_8$ | CH(Ph)$_2$ | Me | 2-carboxybenzamido | H | H | 663(M-18) |
| I-6 | H | cycNC$_5$H$_{10}$ | CH(Ph)$_2$ | Me | 2-carboxybenzamido | H | H | 677(M-18) |
| I-7 | H | cycNC$_4$H$_8$O | CH(Ph)$_2$ | Me | 2-carboxybenzamido | H | H | 679(M-18) |
| I-8 | H | NH$_2$ | CH(Ph)$_2$ | H | 2-carboxybenzamido | H | H | 595(M-18) |
| I-9 | H | NHME | CH(Ph)$_2$ | H | 2-carboxybenzamido | H | H | 609(M-18) |
| I-10 | Et | NMe$_2$ | CH(Ph)$_2$ | Me | 2-carboxybenzamido | H | H | 665(M-18) |
| I-11 | iPr | NMe$_2$ | CH(Ph)$_2$ | Me | 2-carboxybenzamido | H | H | 679(M-18) |
| I-12 | nBu | NMe$_2$ | CH(Ph)$_2$ | Me | 2-carboxybenzamido | H | H | 693(M-18) |
| I-13 | nBu | NMe$_2$ | CH(Ph)$_2$ | Me | 2-carboxybenzamido | Me | Me | 721(m-18) |
| I-14 | nHex | NMe$_2$ | CH(Ph)$_2$ | Me | 2-carboxybenzamido | H | H | 721(M-18) |

The results of elementary analysis of the compounds of Table 6 are shown in Table 7.

TABLE 7

| Compound No. | Elementary analysis | Calcd. for (C, H, N) (%) | | | Found (C, H, N) (%) | | |
|---|---|---|---|---|---|---|---|
| I-1 | C$_{38}$H$_{35}$N$_5$O$_5$ | 71.12, | 5.50, | 10.91 | 71.01, | 5.57, | 10.90 |
| I-2 | C$_{39}$H$_{37}$N$_5$O$_5$ | 71.43, | 5.69, | 10.68 | 71.34, | 5.73, | 10.70 |
| I-3 | C$_{41}$H$_{41}$N$_5$O$_5$ | 72.02, | 6.04, | 10.24 | 71.93, | 6.10, | 10.22 |
| I-4 | C$_{39}$H$_{43}$N$_5$O$_5$ | 70.78, | 6.55, | 10.58 | 70.70, | 6.62, | 10.55 |
| I-5 | C$_{41}$H$_{39}$N$_5$O$_5$ | 72.23, | 5.76, | 10.27 | 72.11, | 5.89, | 10.25 |
| I-6 | C$_{42}$H$_{41}$N$_5$O$_5$ | 72.50, | 5.94, | 10.06 | 72.39, | 6.01, | 10.04 |
| I-7 | C$_{41}$H$_{39}$N$_5$O$_6$ | 70.57, | 5.63, | 10.04 | 70.4S, | 5.71, | 10.06 |
| I-8 | C$_{36}$H$_{31}$N$_5$O$_5$ | 70.46, | 5.09, | 11.41 | 70.33, | 5.20, | 11.39 |
| I-9 | C$_{37}$H$_{33}$N$_5$O$_5$ | 70.80, | 5.30, | 11.16 | 70.70, | 5.44, | 11.15 |
| I-10 | C$_{41}$H$_{41}$N$_5$O$_5$ | 72.02, | 6.04, | 10.24 | 71.90, | 6.15, | 10.26 |
| I-11 | C$_{42}$H$_{43}$N$_5$O$_5$ | 72.29, | 6.21, | 10.03 | 72.15, | 6.35, | 10.06 |
| I-12 | C$_{43}$H$_{45}$N$_5$O$_5$ | 72.55, | 6.37, | 9.84 | 72.44, | 6.48, | 9.88 |
| I-13 | C$_{45}$H$_{49}$N$_5$O$_5$ | 73.05, | 6.67, | 9.46 | 72.94, | 6.78, | 9.45 |
| I-14 | C$_{45}$H$_{49}$N$_5$O$_5$ | 73.05, | 6.67, | 9.46 | 72.98, | 6.77, | 9.47 |

EXAMPLE 10

Process A, Step (10)

Synthesis of (S)-1-((2'-carboxybiphenyl-4-yl)methyl)-N,N-dimethyl-5-diphenylacetyl-4,5,6,7-tetrahydro-1H-imidazo[[4,5-c]pyridine-6-carboxamide (I-15)

Ten ml of ethyl alcohol and 20 ml of a 1N aqueous sodium hydroxide solution were added to (S)-1-((2'-cyanobiphenyl-4-yl) methyl)-N,N-dimethyl-5-diphenylacetyl-4,5,6, 7-tetrahydro-1H-imidazo-[4,5-c]pyridine-6-carboxamide (III-14) (1.9550 g, 0.00337 mol), and the mixture was refluxed under heating for 3 hours, then neutralized with a 6N hydrochloric acid solution, and concentrated. The residue was extracted with chloroform, washed with water, dried over sodium sulfate, and concentrated to obtain a light-yellow foamy material (2.1179 g). This material was purified by silica gel column chromatography (Kieselgel 60, 110 g, chloroform/methanol=50/1) to obtain the objective product (I-15; Compound No. 15) (1.8756 g; yield: 92.9%) as a white foamy material. MS (EI): 580 (M-18).

The compounds of Table 8, including compounds wherein R is 2-(1H-tetrazol-5-yl)phenyl, were synthesized in the similar way. The results of elementary analysis of the compounds of Table 8 are shown in Table 9.

TABLE 8

| Compound No. | R¹ | R²'. | R³ | R⁴ | R | R⁷ | R⁸ | MS(EI) |
|---|---|---|---|---|---|---|---|---|
| I-15 | H | NMe₂ | CH(Ph)₂ | H | 2-carboxy-phenyl | H | H | 580(M−18) |
| I-16 | H | NMe₂ | CH(Ph)₂ | H | 2-(1H-tetrazol-5-yl)phenyl | H | H | 622(M+) |
| I-17 | nBu | NMe₂ | CH(Ph)₂ | H | 2-carboxy-phenyl | H | H | 636(M−18) |
| I-18 | nBu | NMe₂ | CH(Ph)₂ | H | 2-(1H-tetrazol-5-yl)phenyl | H | H | 678(M+) |
| I-19 | nBu | NMe₂ | CH (Ph) 2 | Me | 2-(IH-tetrazol-5-yl)phenyl | H | H | 692(M+) |
| I-20 | nBu | NMe₂ | CH(Ph)₂ | Me | 2-(1H-tetrazol-5-yl)phenyl | Me | Me | 720(M+) |

TABLE 9

| Compound No. | Elementary analysis | Calcd. for (C, H, N) (%) | | | Found (C, H, N) (%) | | |
|---|---|---|---|---|---|---|---|
| I-15 | C₃₇H₃₄N₄O₄ | 74.23, | 5.72, | 9.36 | 74.11, | 5.80, | 9.35 |
| I-16 | C₃₇H₃₄N₈O₂ | 71.36, | 5.50, | 17.99 | 71.30, | 5.55, | 17.97 |
| I-17 | C₄₁H₄₂N₄O₄ | 75.20, | 6.46, | 8.56 | 75.11, | 6.50, | 8.54 |
| I-18 | C₄₁H₄₂N₈O₂ | 72.54, | 6.23, | 16.51 | 2.49, | 6.30, | 16.48 |
| I-19 | C₄₂H₄₄N₈O₂ | 72.81, | 6.40, | 16.1 | 72.77, | 6.49, | 16.15 |
| I-20 | C₄₄H₄₈N₈O₂ | 73.31, | 6.71, | 15.54 | 73.26, | 6.78, | 15.50 |

EXAMPLE 11

Process B, Step (a)

Synthesis of (S)-2-triphenylmethylamino-3-(1-triphenylmethylimidazol-5-yl)propanoic acid methyl ester (XXII)

Triethylamine (145 ml, 1.038 mol) was added to a solution of the compound (XXIII) (50.25 g, 0.208 mol) and TrCl (138.90 g, 0.498 mol) in CH₂Cl₂ (500 ml) dropwise with stirring under ice cooling for 30 minutes, followed by 6-hour stirring at room temperature. The reaction mixture was poured into water and extracted with CH₂Cl₂. The organic layer was washed with a saturated NaCl aqueous solution, dried over Na₂SO₄, and concentrated to obtain a crude product (168.87 g) as a yellow oily material. This crude product was purified by silica gel column chromatography (hexane/acetone=3/1) to obtain the objective compound (XXII) (119.934 g; yield: 88.4%) as a white foamy material.

¹H-NMR (CDCl₃) δ: 2.71 (d, 1H, J=10.5 Hz, NH), 2.78 (dd, 1H, J=6.9, 13.8 Hz), 2.96 (dd, 1H, J=6.9, 13.8 Hz), 3.05 (s, 3H), 3.66 (dt, 1H, J=6.9, 10.5 Hz), 6.62 (s, 1H), 7.11–7.15 (m, 9H), 7.18–7.21 (m, 6H), 7.26–7.32 (m, 9H), 7.36 (s, 1H), 7.43 (d-like, 6H, J=7.3 Hz).

IR (ν_max, KBr): 3480, 1748, 1509, 1455, 1163, 748, 705 cm⁻¹.

EXAMPLE 12

Process B, Step (b)

Synthesis of (S)-2-triphenylmethylamino-3-(1-triphenylmethylimidazol-5-yl) propanol (XXI)

The compound (XXII) (58.917 g, 0.0901 mol) was added to a suspension of LiAlH₄ (6.839 g, 0.180 mol) in dry Et₂O (590 ml) over a period of 2.5 hours. The mixture was stirred under ice cooling for one hour, and then Na₂SO₄·10H₂O was added to the resulting solution to dispose of the excess LiAlH₄, followed by filtration with Celite 545. The filtrate was concentrated and the residue was diluted with CHCl₃, washed with a saturated NH₄Cl aqueous solution and a saturated NaCl aqueous solution, then dried over Na₂SO₄, and concentrated to obtain the objective compound (56.390 g; yield: 100%) as a white foamy material.

¹H-NMR (CDCl₃) δ: 1.90 (b, 1H, NH), 1.95 (dd, 1H, J=6.4, 14.7 Hz), 2.38 (dd, 1H, J=3.2, 14.7 Hz), 2.91 (b, 1H), 2.99 (dd, 1H, J=6.4, 11.5 Hz), 3.47 (dd, 1H, J=3.2, 11.5 Hz), 4.95 (b, 1H, OH), 6.29 (s, 1H), 7.09–7.20 (m, 15H), 7.26–7.33 (m, 10H), 7.48–7.49 (m, 6H).

IR (ν_max, KBr): 3480, 1550, 1455, 1036, 746, 702 cm⁻¹.

EXAMPLE 13

Process B, Step (c)

Synthesis of (S)-1-t-butyldimethylsilyloxy-2-triphenylmethylamino-3-(1-triphenylmethylimidazol-5-yl)propane (xx)

Imidazole (12.269 g, 0.180 mol) and tert-butyldimethylsilyl chloride (TBDMSCl) (20.37 g, 0.135 mol) were added to a solution of the compound (XXI) (56.390 g, 0.0901 mol) in dry DMF (560 ml) under ice cooling, and the mixture was stirred at room temperature for 3.5 hours. The reaction mixture was poured into water, extracted with Et₂O, washed with water and a saturated NaCl aqueous solution, then dried over Na₂SO₄, and concentrated to obtain a light-yellow foamy material (67.602 g). This crude product was purified by silica gel column chromatography (hexane/acetone=5/1) to obtain the objective compound (XX) (58.770 g; yield: 88.1%) as a white foamy material.

¹H-NMR (CDCl₃) δ: −0.13 (s, 6H), 0.80 (s, 9H), 1.60 (b, 1H, NH), 2.19 (dd, 1H, J=7.6, 14.2 Hz), 2.57 (dd, 1H, J=4.1, 14.2 Hz), 2.73 (b, 1H), 2.89 (dd, 1H, J=6.0, 9.6 Hz), 3.27 (dd, 1H, J=4.1, 9.6 Hz), 5.35 (s, 2H), 6.38 (s, 1H), 7.12–7.35 (m, 25H), 7.56 (d-like, 6H, J=7.3 Hz).

IR (ν_max, KBr): 3100, 2990, 2970, 2925, 2890, 1508, 1480, 1455, 1253, 1132, 1090, 1072, 1035, 900, 830, 770, 742, 700, 658, 636 cm⁻¹.

EXAMPLE 14

Process B, Step (d)

Synthesis of (S)-1-t-butyldimethylsilyloxy-2-triphenylmethylamino-3-(2-n-butyl-1-triphenylmethylimidazol-5-yl)propane (XIX-3)

A 1.5N nBuLi/hexane mixed solution (61.0 ml, 0.0914 mol) was added dropwise to a solution of the compound (XX) (22.557 g, 0.0305 mol) in dry Et₂O (340 ml) over a period of 15 minutes by using an injector. Three minutes thereafter, nBuI (5.2 ml, 0.0457 mol) and HMPA (38 ml) were added dropwise with an injector under the same conditions. After 20-minute stirring, the mixture was heated to room temperature and further stirred for 4 hours. The reaction mixture was poured into water and extracted with EtOAc. The organic layer was washed with a saturated NaCl solution, then dried over $Na_2SO_4$, and concentrated to obtain a yellow oily material (25.830 g; yield: 100% up). This material was purified by silica gel column chromatography (hexane/acetone=20/1) to obtain the objective compound (XIX-3) (10.710 g; yield: 44.1%) as a light-yellow foamy material.

$^1$H-NMR ($CD_2Cl_2$) δ: −0.136, −0.144 (each s, each 3H), 0.58 (t, 3H, J=7.3 Hz), 0.77 (s, 9H), 0.89 (sext, 2H, J=7.3 Hz), 1.01 (m, 1H), 1.12 (m, 1H), 1.78 (m, 2H), 1.98 (dd, 1H, J=6.7, 14.0 Hz), 2.43 (dd, 1H, J=4.8, 14.0 Hz), 2.57 (b, 1H, CH), 3.06 (dd, 1H, J=6.9, 9.6 Hz), 3.10 (b, 1H, NH), 3.28 (dd, 1H, J=4.4, 9.6 Hz), 6.19 (s, 1H), 7.06–7.54 (m, 30H).

IR ($ν_{max}$, KBr): 3500, 3000, 2975, 2905, 1510, 1459, 1408, 1260, 1160, 1093, 1075, 1038, 834, 775, 746, 702, 640 $cm^{-1}$.

There were similarly synthesized the compounds of Table 10.

TABLE 10

| Compound No. | $R^1$ | Elementary analysis | Calcd. for (C, H, N) (%) | | | Found (C, H, N) (%) | | | MS(EI) |
|---|---|---|---|---|---|---|---|---|---|
| XIX-1 | nPr | $C_{53}H_{59}N_3OSi$ | 81.39, | 7.60, | 5.37 | 81.50, | 7.48, | 5.30 | 782(M$^+$) |
| XIX-2 | iPr | $C_{53}H_{59}N_3OSi$ | 81.39, | 7.60, | 5.37 | 81.47, | 7.52, | 5.29 | 782(M$^+$) |
| XIX-3 | nBu | $C_{54}H_{61}N_3OSi$ | 81.46, | 7.72, | 5.28 | 81.61, | 7.69, | 5.19 | 796(M$^+$) |
| XIX-4 | nHex | $C_{56}H_{65}N_3OSi$ | 82.61, | 8.05, | 5.16 | 82.76, | 7.98, | 5.09 | 814(M$^+$) |

EXAMPLE 15

Process B, Step (e)

Synthesis of (S)-2-amino-3-(2-n-butyl-1H-imidazol-5-yl)propanol (XVIII-3) and (S)-2-n-butyl-4,5,6,7-tetrahydro-1H-imidazo[4,5-c]pyridine-6-methanol hydrochloride (XVII-3)

A 1N HCl aqueous solution (140 ml) and a 37% HCHO aqueous solution (3.6 ml) were added to the compound (XIX-3) (11.745 g, 0.0148 mol) and the mixture was stirred first at room temperature for 40 minutes and then in a 120° C. oil bath for 4 hours. The reaction mixture was cooled and the insoluble portion was filtered out, followed by washing with water. The aqueous layer was washed with $Et_2O$, then concentrated, and dried to obtain the objective compound (XVII-3) (4.0370 g; yield: 97.0%) as a yellow solid.

$^1$H-NMR ($D_2O$) δ: 0.95 (t, 3H, J=7.3 Hz), 1.40 (sext, 2H, J=7.3 Hz), 1.79 (quint, 2H, J=7.3 Hz), 3.02 (t, 2H, J=7.3 Hz), 3.12 (d-like, 1H, J=4.6 Hz), 3.16 (bs, 1H), 3.85–3.90 (m, 2H), 4.08 (d-like, 1H, J=9.2 Hz), 4.48 (d, 1H, J=15.4 Hz), 4.52 (d, 1H, J=15.4 Hz).

IR ($ν_{max}$, KBr): 3410, 2950, 1675, 1620, 1560, 1430, 1065 $cm^{-1}$.

The compounds shown in Table 11 were similarly synthesized.

TABLE 11

| Compound No. | $R^1$ | MS (EI) |
|---|---|---|
| XVII-1 | nPr | 195 (M-2HCl) |
| XVII-2 | nhex | 195 (M-2HCl) |
| XVII-3 | nBu | 209 (M-2HCl) |
| XVII-4 | nhex | 237 (M-2HCl) |

By using the compound (XIX-3) (1.7750 g, 0.00223 mol) and an 1N HCl aqueous solution (18 ml), the above reaction procedure was followed without adding the 37% HCHO aqueous solution to obtain the objective compound (XVIII-3) (0.7003 g; yield: 99.6%) as a yellow viscous material.

$^1$H-NMR ($D_2O$) δ: 0.96 (t, 3H, J=7.3 Hz), 1.39 (sext, 2H, J=7.3 Hz), 1.80 (quint, 2H, J=7.3 Hz), 3.00 (t, 2H, J=7.3 Hz), 2.8–3.3 (m, 3H), 3.7–4.3 (m, 2H), 6.05 (bs, 1H).

MASS (EI): 197 (M-2HCl).

There were similarly synthesized the compounds shown in Table 12.

TABLE 12

| Compound No. | $R^1$ | MASS (EI) |
|---|---|---|
| XVIII-1 | nPr | 183 (M-2HCl) |
| XVIII-2 | iPr | 183 (M-2HCl) |
| XVIII-3 | nBu | 197 (M-2HCl) |
| XVIII-4 | nHex | 225 (M-2HCl) |

EXAMPLE 16

Process B, Step (f)

Synthesis of (S)-2-n-butyl-5-diphenylacetyl-4,5,6,7-tetrahydro-1H-imidazo[4,5-c]pyridine-6-methanol (XVI-4)

Diphenylacetic acid (14.6617 g, 0.069 mol), N,N′-dicyclohexylcarbodiimide (DCCI) (14.2528 g, 0.069 mol), and 1-hydroxybenzotriazole (HBTA) (9.3345 g, 0.069 mol) were dissolved in dry THF (61 ml) and stirred at room temperature for 20 minutes. A solution of the compound (XVII-3) (6.0920 g, 0.0216 mol) in dry THF (30 ml) and dry triethylamine (TEA) (6.0 ml, 0.043 mol) were added to this solution, followed by stirring at room temperature for 14 hours. The insoluble portion was filtered out and washed with THF. The filtrate and washings were joined and concentrated to obtain a crude oily material (11.0015 g). This material was dissolved in a 1/1 mixture (100 ml) of THF and MeOH, after addition of a 1N HCl aqueous solution (25 ml), left as it was for 8 hours. Then, to the mixture added a 1/1 mixture (100 ml) of THF and MeOH and a 1N NaOH solution (50 ml), and the mixture was left as it was for 10 hours. The reaction mixture was concentrated. White crystals were precipitated by addition of $H_2O$ (50 ml). These crystals were washed with water and then vacuum dried to give the compound (XVI-4) (2.1518 g; m.p. 199°-202° C.; yield: 24.7%).

$^1$H-NMR ($CDCl_3$) δ: 0.90, 0.91 (each t, 3H, J=7.3 Hz), 1.30–1.38 (m, 2H), 1.40–1.90 (b, 1H, OH), 1.55–1.70 (m, 2H), 2.55–2.62 (m, 2H), 2.33, 2.81 (s-like, dd, 2H), 3.43–3.58 (m, 2H), 3.86–4.08 (each d, 1H, J=16.7, 15.4 Hz), 4.47, 4.70 (bs, d, 2H, J=16.7 Hz), 5.28, 5.32, 5.51 (d, s, s, 2H, J=16.7 Hz), 7.10–7.60 (m, 10H), 8.80 (b, 1H, NH).

IR ($ν_{max}$, KBr): 3425, 2970, 2930, 2860, 1620, 1450, 1420, 740, 695 $cm^{-1}$.

The compounds shown in Table 13 were similarly synthesized.

TABLE 13

| Compound No. | $R^1$ | $R^3$ | Elementary analysis | Calcd. for (C, H, N) (%) | | | Found (C, H, N) (%) | | | MS(EI) |
|---|---|---|---|---|---|---|---|---|---|---|
| XVI-1 | H | (Ph)$_2$CH | $C_{21}H_{21}N_3O_2$ | 72.76, | 6.09, | 12.09 | 72.78, | 5.89, | 12.00 | 347(M$^+$) |
| XVI-2 | nPr | (Ph)$_2$CH | $C_{24}H_{27}N_3O_2$ | 74.01, | 6.99, | 10.79 | 74.16, | 6.83, | 10.70 | 389(M$^+$) |
| XVI-3 | iPr | (Ph)$_2$CH | $C_{24}H_{27}N_3O_2$ | 74.01, | 6.99, | 10.79 | 74.21, | 6.90, | 10.69 | 389(M$^+$) |
| XVI-4 | nBu | (Ph)$_2$CH | $C_{25}H_{29}N_3O_2$ | 74.41, | 7.24, | 10.41 | 74.57, | 7.20, | 10.30 | 404(M$^+$) |
| XVI-5 | nBu | (Ph)(c-Hex)CH | $C_{25}H_{35}N_3O_2$ | 73.31, | 8.61, | 10.26 | 73.49, | 8.55, | 10.19 | 410(M$^+$) |
| XVI-6 | nHex | (Ph)$_2$CH | $C_{27}H_{33}N_3O_2$ | 75.14, | 7.71, | 9.74 | 75.30, | 7.68, | 9.67 | 432(M$^+$) |

EXAMPLE 17

Process B, Step (g)

Synthesis of (S)-2-n-butyl-1-[(4-methoxycarbonylphenyl)methyl]-5-diphenylacetyl-4,5,6,7-tetrahydro-1H-imidazo[4,5-c]pyridine-6-methanol (XV-8)

Methyl 4-(bromomethyl)benzoate (0.0334 g, 0.00015 mol) and K$_2$CO$_3$ (0.0201 g, 0.00015 mol) were added to a solution of the compound (XVI-4) (0.0491 g, 0.00012 mol) in dry DMF (0.49 ml), and the mixture was stirred vigorously at room temperature for 24 hours. The reaction mixture was poured into water, extracted with EtOAc, washed with water, then dried over Na$_2$SO$_4$, and concentrated to obtain a light-yellow oily material (0.0656 g). This crude oily product was purified by silica gel column chromatography (hexane/acetone=1/2) to obtain the objective compound (XV-8) (0.0211 g), its 3-position isomer (0.0262 g), and a mixture of them (0.0035 g), each as a white foamy material (yield: 75.7%). The structures of the two compounds were determined by an NOE difference spectrum.

$^1$H-NMR (CDCl$_3$) δ: 0.86, 0.87 (each, t, 3H, J=7.3 Hz), 1.28–1.36 (m, 2H), 1.58–1.65 (m, 3H, CH$_3$CH$_2$CH$_2$CH$_2$—, CH$_2$OH), 1.99–2.63 (m, 2H), 2.52–2.63 (m, 2H), 3.31–3.57 (m, 2H, CH$_2$OH), 3.92, 3.93 (each, s, 3H), 3.90, 4.13, 4.76, 5.42 (each, d, 2H, J=15.4 Hz), 4.40–4.47, 5.26–5.30 (each, m, 1H), 4.94, 5.02 (each, s, 2H), 5.35, 5.43 (each s, 1H), 6.91–6.99 (m, 2H), 7.17–7.32 (m, 10H), 7.98–8.01 (m, 2H).

IR ($v_{max}$, KBr): 3460, 1725, 1640, 1453, 1430, 1415, 1280, 1110, 743, 700 cm$^{-1}$.

EXAMPLE 18

Process B, Step (g)

Synthesis of (S)-2-n-butyl-1-[(2'-cyanobiphenyl-4-yl)methyl]-5-diphenylacetyl-4,5,6,7-tetrahydro-1H-imidazo[4,5-c]pyridine-6-methanol (XV-10)

4'-(bromomethyl)-2-cyanobiphenyl (2.3655 g, 0.0869 mol) and K$_2$CO$_3$ (1.9222 g, 0.0139 mol) were added to a solution of the compound (XVI-4) (2.8060 g, 0.00695 mol) in dry DMF (28 ml), and the mixture was stirred vigorously at room temperature for 23 hours. The reaction mixture was poured into water, extracted with EtOAc, washed with water, dried over Na$_2$SO$_4$, and concentrated to obtained a light-yellow foamy material (4.5301 g). This material was purified by silica gel column chromatography to obtain the compound (XV-10) (0.9288 g), its 3-position isomer (1.4733 g), and a mixture of them (0.0207 g) (yield: 58.6%). The structures of the two compounds were determined by an NOE difference spectrum.

$^1$H-NMR (CDCl$_3$) δ: 0.89, 0.90 (each t, 3H, J=7.3 Hz), 1.36 (sext, 2H, J=7.3 Hz), 1.64–1.78 (m, 2H), 1.88 (bs, 1H, OH), 2.14, 2.72 (each dd, 1H, J=6.0, 15.6 Hz), 2.21, 2.51 (each d, 1H, J=15.6 Hz), 2.60–2.67 (m, 2H), 3.35–3.62 (m, 2H, CH$_2$OH), 3.96, 4.93 (each d, 1H, J=17.0 Hz), 4.12, 4.78 (each d, 1H, J=15.6 Hz), 4.47–4.51, 5.35–5.40 (each m, 1H), 5.06–5.13 (m, 2H), 5.36, 5.42 (each s, 1H), 6.93–7.10 (m, 2H), 7.15–7.39 (m, 10H), 7.40–7.58 (m, 4H), 7.60–7.82 (m, 2H).

IR ($v_{max}$, KBr): 3425, 2960, 2925, 2860, 1637, 1500, 1480, 1450, 1410, 1375, 760, 740, 700 cm$^{-1}$.

There were similarly synthesized the compounds shown in Table 14.

TABLE 14

| Compound No. | $R^1$ | $R^3$ | $R^4$ | $R^7$ | $R^8$ | $R^6$ | Elementary analysis | Calcd. for (C, H, N) (%) | | | Found (C, H, N) (%) | | | MS(EI) |
|---|---|---|---|---|---|---|---|---|---|---|---|---|---|---|
| XV-1 | H | (Ph)$_2$CH | H | H | H | COOMe | $C_{30}H_{29}N_3O_4$ | 72.71, | 5.90, | 8.48 | 72.90, | 5.79, | 8.40 | 496(M$^+$) |
| XV-2 | H | (Ph)$_2$CH | H | Me | Me | COOMe | $C_{32}H_{33}N_3O_4$ | 73.40, | 6.35, | 8.02 | 73.51, | 6.30, | 7.99 | 524(M$^+$) |
| XV-3 | H | (Ph)$_2$CH | Me | H | H | NO$_2$ | $C_{29}H_{28}N_4O_4$ | 70.15, | 5.68, | 11.28 | 70.30, | 5.60, | 11.22 | 497(M$^+$) |
| XV-4 | H | (Ph)$_2$CH | H | H | H | 2-CN-Ph | $C_{35}H_{30}N_4O_2$ | 78.04, | 5.61, | 10.40 | 78.20, | 5.54, | 10.33 | 539(M$^+$) |
| XV-5 | H | (Ph)$_2$CH | H | H | H | 2-(1-Tr-1H-tetrazol-5-yl)Ph | $C_{54}H_{45}N_7O_2$ | 78.71, | 5.50, | 11.90 | 78.89, | 5.40, | 11.83 | 824(M$^+$) |
| XV-6 | nPr | (Ph)$_2$CH | H | H | H | 2-CN-Ph | $C_{38}H_{36}N_4O_2$ | 78.59, | 6.25, | 9.65 | 78.71, | 6.19, | 9.58 | 581(M$^+$) |
| XV-7 | iPr | (Ph)$_2$CH | H | H | H | 2-CN-Ph | $C_{38}H_{36}N_4O_2$ | 78.59, | 6.25, | 9.65 | 78.66, | 6.21, | 9.63 | 581(M$^+$) |
| XV-8 | nBu | (Ph)$_2$CH | H | H | H | COOMe | $C_{34}H_{37}N_3O_4$ | 74.02, | 6.76, | 7.62 | 74.21, | 6.66, | 7.59 | 552(M$^+$) |
| XV-9 | nBu | (Ph)$_2$CH | Me | H | H | NO$_2$ | $C_{34}H_{38}N_4O_4$ | 72.06, | 6.76, | 9.89 | 72.25, | 6.64, | 9.78 | 567(M$^+$) |
| XV-10 | nBu | (Ph)$_2$CH | H | H | H | 2-CN-Ph | $C_{39}H_{38}N_4O_2$ | 78.76, | 6.44, | 9.42 | 78.91, | 6.38, | 9.39 | 595(M$^+$) |
| XV-11 | nBu | (Ph)$_2$CH | H | H | H | 2-(1-Tr-1H-tetrazol-5-yl)Ph | $C_{58}H_{53}N_7O_2$ | 79.15, | 6.07, | 11.14 | 79.30, | 5.98, | 11.07 | 880(M$^+$) |
| XV-12 | nBu | (Ph)(c-Hex)CH | H | H | H | 2-CN-Ph | $C_{39}H_{44}N_4O_2$ | 77.97, | 7.38, | 9.33 | 78.10, | 7.29, | 9.30 | 601(M$^+$) |
| XV-13 | nHex | (Ph)$_2$CH | H | H | H | 2-CN-Ph | $C_{41}H_{42}N_4O_2$ | 79.07, | 6.80, | 9.00 | 79.22, | 6.77, | 8.95 | 623(M$^+$) |

EXAMPLE 19

Process B, Step (h)

Synthesis of
(S)-2-n-butyl-1-[(4-methoxycarbonylphenyl)methyl]-5-diphenylacetyl-4,5,6,7-tetrahydro-1H-imidazo[4,5-c]pyridine-6-carboxylic acid (XIV-8)

$CrO_3$ (0.33 g) was dissolved in $H_2O$ (0.62 ml), and concentrated $H_2SO_4$ was slowly added dropwise thereto. The resultantly produced salt was dissolved in $H_2O$ (0.1 ml) to prepare an oxidizing reagent. Meanwhile, the compound (XV-8) (0.2916 g) was dissolved in acetone (4.4 ml), and the previously prepared oxidizing reagent was added dropwise thereto at room temperature until the orangish red color did not fade away. After 30-minute stirring, iPrOH was added to the reaction mixture until it assumed a green color, and then the mixture was concentrated. The resulting crude product was purified by silica gel column chromatography ($CHCl_3$/MeOH=8/1) to obtain the objective compound (XIV-8) (0.1883 g; m.p. 177°–180° C.; yield: 63.0%).

$^1$H-NMR ($CDCl_3$) δ: 0.79, 0.83 (each t, 3H, J=7.3 Hz), 1.18–1.28 (m, 2H), 1.40–1.55 (m, 2H), 1.77, 2.99, 3.24–3.44 (m, d, m, 2H, J=14.7 Hz), 2.45–2.70 (m, 2H), 3.89, 3.92 (each s, 3H), 4.28, 4.57, 4.69, 5.07 (each d, 2H, J=14.7 Hz), 5.17–5.27 (m, 2H), 5.51, 5.55 (each s, 1H), 5.51–5.55, 5.70 (d, 1H, J=5.5 Hz), 7.09–7.45 (m, 12H), 7.90–8.10 (m, 2H).

IR ($v_{max}$, KBr): 3470, 2980, 1726, 1640, 1615, 1506, 1455, 1435, 1417, 1283, 1190, 1112, 750, 700 cm$^{-1}$.

EXAMPLE 20

Process B, Step (h)

Synthesis of
(S)-2-n-butyl-1-[(2'-cyanobiphenyl-4-yl)methyl]-5-diphenylacetyl-4,5,6,7-tetrahydro-1H-imidazo[4,5-c]pyridine-6-carboxylic acid (XIV-10)

The oxidizing reagent (0.9 ml) as prepared in Example 19 was added dropwise to a solution of the compound (XV-10) (0.6249 g, 0.00105 mol) in acetone (9.4 ml) at room temperature. After 30-minute stirring, iPrOH was added to the reaction mixture until it assumed a green color, and then the mixture was concentrated. The resulting crude product was purified by silica gel column chromatography ($CHCl_3$/MeOH=6/1) to obtain the compound (XIV-10) (0.3619 g; yield: 56.6%) as a white foamy material.

$^1$H-NMR ($CDCl_3$) δ: 0.75–1.06 (m, 3H), 1.15–1.40 (m, 2H), 1.44–1.70 (m, 2H), 2.46–2.64 (m, 2H), 2.69, 2.93 (each dd, 1H, J=6.0, 15.6 Hz), 3.08, 3.31 (each d, 1H, J=15.6 Hz), 4.27, 4.67 (each d, 1H, J=15.6 Hz), 4.58, 4.99 (each d, 1H, J=15.6 Hz), 4.94–5.25 (m, 2H), 5.32, 5.43 (each s, 1H), 4.83, 5.68 (each d, 1H, J=6.0 Hz), 7.02–7.85 (m, 18H).

IR ($v_{max}$, KBr) $v_{max}$: 3425, 2960, 1620, 1500, 1408, 758, 742, 700, 630, 560 cm$^{-1}$.

There were similarly synthesized the compounds shown in Table 15.

TABLE 15

| Compound No. | $R^1$ | $R^3$ | $R^4$ | $R^7$ | $R^8$ | $R^6$ | Elementary analysis | Calcd. for (C, H, N) (%) | | | Found (C, H, N) (%) | | | MS (FAB) |
|---|---|---|---|---|---|---|---|---|---|---|---|---|---|---|
| XIV-1 | H | (Ph)$_2$CH | H | H | H | COOMe | $C_{30}H_{27}N_3O_5$ | 70.71, | 5.34, | 8.25 | 70.89, | 5.29, | 8.18 | 510(M$^+$) |
| XIV-2 | H | (Ph)$_2$CH | H | Me | Me | COOMe | $C_{32}H_{31}N_3O_5$ | 71.49, | 5.81, | 7.82 | 71.63, | 5.77, | 7.74 | 538(M$^+$) |
| XIV-3 | H | (Ph)$_2$CH | Me | H | H | NO$_2$ | $C_{29}H_{26}N_4O_5$ | 68.22, | 5.13, | 10.97 | 68.40, | 5.09, | 10.88 | 511(M$^+$) |
| XIV-4 | H | (Ph)$_2$CH | H | H | H | 2-CN-Ph | $C_{35}H_{28}N_4O_3$ | 76.07, | 5.11, | 10.14 | 76.21, | 5.04, | 10.07 | 553(M$^+$) |
| XIV-5 | H | (Ph)$_2$CH | H | H | H | 2-(1-Tr-1H-tetrazol-5-yl)Ph | $C_{54}H_{43}N_7O_3$ | 77.40, | 5.17, | 11.70 | 77.55, | 5.09, | 11.65 | 838(M$^+$) |
| XIV-6 | nPr | (Ph)$_2$CH | H | H | H | 2-CN-Ph | $C_{38}H_{34}N_4O_3$ | 76.75, | 5.76, | 9.42 | 76.91, | 5.65, | 9.38 | 595(M$^+$) |
| XIV-7 | iPr | (Ph)$_2$CH | H | H | H | 2-CN-Ph | $C_{38}H_{34}N_4O_3$ | 76.75, | 5.76, | 9.42 | 76.88, | 5.59, | 9.40 | 595(M$^+$) |
| XIV-8 | nBu | (Ph)$_2$CH | H | H | H | COOMe | $C_{34}H_{35}N_3O_5$ | 72.19, | 6.24, | 7.43 | 72.30, | 6.20, | 7.38 | 566(M$^+$) |
| XIV-9 | nBu | (Ph)$_2$CH | Me | H | H | NO$_2$ | $C_{34}H_{36}N_4O_5$ | 70.33, | 6.25, | 9.65 | 70.50, | 6.19, | 9.62 | 581(M$^+$) |
| XIV-10 | nBu | (Ph)$_2$CH | H | H | H | 2-CN-Ph | $C_{39}H_{36}N_4O_3$ | 76.95, | 5.96, | 9.20 | 77.09, | 5.88, | 9.14 | 609(M$^+$) |
| XIV-11 | nBu | (Ph)$_2$CH | H | H | H | 2-(1-Tr-1H-tetrazol-5-yl)Ph | $C_{58}H_{51}N_7O_3$ | 77.92, | 5.75, | 10.97 | 80.10, | 5.64, | 10.85 | 894(M$^+$) |
| XIV-12 | nBu | (Ph)(c-Hex)CH | H | H | H | 2-CN-Ph | $C_{39}H_{42}N_4O_3$ | 76.19, | 6.89, | 9.11 | 76.33, | 6.75, | 9.08 | 615(M$^+$) |
| XIV-13 | nHex | (Ph)$_2$CH | H | H | H | 2-CN-Ph | $C_{41}H_{40}N_4O_3$ | 77.33, | 6.33, | 8.80 | 77.21, | 6.54, | 8.65 | 637(M$^+$) |

EXAMPLE 21

Process B, Step (i)

Synthesis of
4-[[(S)-2-butyl-1-[(4-methoxycarbonylphenyl)methyl]-5-diphenylacetyl-4,5,6,7-tetrahydro-1H-imidazo[4,5-c]pyridin-6-yl]carbonyl]morpholine (XIII-8)

The compound (XIV-8) (0.1315 g, 0.00023 mol), DCCI (0.0624 g, 0.0003 mol), HBTA (0.0377 g, 0.00028 mol), and morpholine (0.024 ml, 0.00028 mol) were dissolved in dry THF (2.0 ml) and stirred at room temperature for 19 hours. The insoluble portion was filtered out and washed with THF. The filtrate and washings were joined and concentrated to obtain a crude oily product (0.3010 g). This crude product was purified by silica gel column chromatography ($CHCl_3$/MeOH=60/1) to obtain a white foamy material (0.1204 g). This material was again purified by using a preparative TLC plate (0.5 mm thick, 20 cm×20 cm; developing solvent: hexane/acetone=2/3) to obtain the objective compound (XIII-8) (0.0911 g; yield: 61.7%).

$^1$H-NMR ($CDCl_3$) δ: 0.84 (t, 3H, J=7.3 Hz), 1.28 (sext, 2H, J=7.3 Hz), 1.58 (quint, 2H, J=7.3 Hz), 2.49 (t, 2H, J=7.3 Hz), 2.70 (dd, 1H, J=6.0, 15.1 Hz), 2.80 (d, 1H, J=15.1 Hz), 3.25–3.70 (b, 8H), 3.92 (s, 3H), 4.26 (d, 1H, J=15.1 Hz), 4.90 (d, 1H, J=15.1 Hz), 5.02, 5.07 (each d, each 1H, J=17.4 Hz), 5.35 (s, 1H), 5.96 (d, 1H, J=6.0 Hz), 7.09 (d, 2H, J=8.3 Hz), 7.17–7.35 (m, 10H), 8.02 (d, 2H, J=8.3 Hz).

IR ($v_{max}$, KBr): 3460, 1725, 1645, 1455, 1433, 1415, 1280, 1230, 1113, 750, 700 cm$^{-1}$.

EXAMPLE 22

Process B, Step (i)

Synthesis of 4-[[(S)-2-butyl-1-[(2'-cyanobiphenyl-4-yl)methyl]-5-diphenylacetyl-4,5,6,7-tetrahydro-1H-imidazo[4,5-c]pyridin-6-yl]carbonyl]morpholine (XIII-10)

The compound (XIV-10) (0.3301 g, 0.000542 mol), DCCI (0.1455 g, 0.000705 mol), HBTA (0.0953 g, 0.000705 mol), and morpholine (0.06 ml, 0.000705 mol) were dissolved in dry THF (5.0 ml) and stirred at room temperature for 48 hours. The insoluble portion was filtered out and washed with THF. The filtrate and washings were joined and concentrated to obtain a crude product (0.5500 g). This crude product was purified by silica gel column chromatography (hexane/acetone=2/3) to obtain the objective compound (XIII-10) (0.1764 g; yield: 48.0%) as a white foamy material.

$^1$H-NMR (CDCl$_3$) δ: 0.87 (t, 3H, J=7.3 Hz), 1.32 (sext, 2H, J=7.3 Hz), 1.64 (quint, 2H, J=7.3 Hz), 2.55 (t, 2H, J=7.3 Hz), 2.77 (dd, 1H, J=6.0, 15.1 Hz), 2.86 (d, 1H, J=15.1 Hz), 3.20–3.80 (b, 8H), 4.29 (d, 1H, J=15.6 Hz), 4.90 (d, 1H, J=15.6 Hz), 5.04 (d, 1H, J=17.0 Hz), 5.09 (d, 1H, J=17.0 Hz), 5.37 (s, 1H), 5.99 (d, 1H, J=6.0 Hz), 7.20–7.85 (m, 18H).

IR ($\nu_{max}$, KBr): 3430, 1640, 1450, 1408, 1228, 1113, 760, 700 cm$^{-1}$.

MS (EI): 678 (M+):

The compounds shown in Tables 16 and 17 were similarly synthesized.

TABLE 16

| Compound No. | R$^1$ | R$^3$ | R$^4$ | R$^7$ | R$^8$ | R$^6$ | R$^{2'}$ | Elementary analysis | Calcd. for (C, H, N) (%) | Found (C, H, N) (%) | MS (EI) |
|---|---|---|---|---|---|---|---|---|---|---|---|
| XIII-1 | H | (Ph)$_2$CH | H | H | H | COOMe | 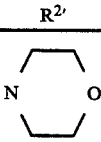 | C$_{34}$H$_{34}$N$_4$O$_5$ | 70.57, 5.92, 9.68 | 70.70, 5.88, 9.60 | 579 (M+) |
| XIII-2 | H | (Ph)$_2$CH | H | Me | Me | COOMe | 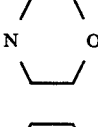 | C$_{36}$H$_{38}$N$_4$O$_5$ | 71.27, 6.31, 9.23 | 71.43, 6.18, 9.21 | 607 (M+) |
| XIII-3 | H | (Ph)$_2$CH | Me | H | H | NO$_2$ | 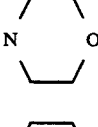 | C$_{33}$H$_{33}$N$_5$O$_5$ | 68.38, 5.74, 12.08 | 68.51, 5.65, 11.98 | 580 (M+) |
| XIII-4 | H | (Ph)$_2$CH | H | H | H | 2-CN-Ph | 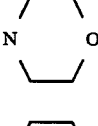 | C$_{39}$H$_{35}$N$_5$O$_3$ | 75.34, 5.67, 11.26 | 75.51, 5.59, 11.18 | 622 (M+) |
| XIII-5 | H | (Ph)$_2$CH | H | H | H | 2-(1-Tr-1H-tetrazol-5-yl)Ph | 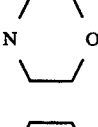 | C$_{58}$H$_{50}$N$_8$O$_3$ | 76.80, 5.56, 12.35 | 76.96, 5.49, 12.24 | 907 (M+) |
| XIII-6 | nPr | (Ph)$_2$CH | H | H | H | 2-CN-Ph | 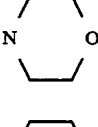 | C$_{42}$H$_{41}$N$_5$O$_3$ | 75.99, 6.23, 10.55 | 76.10, 6.19, 10.48 | 664 (M+) |
| XIII-7 | iPr | (Ph)$_2$CH | H | H | H | 2-CN-Ph | 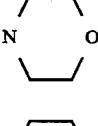 | C$_{42}$H$_{41}$N$_5$O$_3$ | 75.99, 6.23, 10.55 | 76.15, 6.16, 10.48 | 664 (M+) |
| XIII-8 | nBu | (Ph)$_2$CH | H | H | H | COOMe | 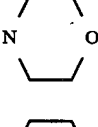 | C$_{38}$H$_{42}$N$_4$O$_5$ | 71.90, 6.67, 8.83 | 72.05, 6.58, 8.79 | 635 (M+) |
| XIII-9 | nBu | (Ph)$_2$CH | Me | H | H | NO$_2$ | 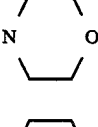 | C$_{37}$H$_{41}$N$_5$O$_5$ | 69.90, 6.50, 11.02 | 70.09, 6.44, 10.95 | 636 (M+) |
| XIII-10 | nBu | (Ph)$_2$CH | H | H | H | 2-CN-Ph | 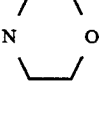 | C$_{43}$H$_{43}$N$_5$O$_3$ | 76.19, 6.39, 10.33 | 76.31, 6.28, 10.21 | 678 (M+) |

TABLE 16-continued

| Compound No. | R¹ | R³ | R⁴ | R⁷ | R⁸ | R⁶ | R²' | Elementary analysis | Calcd. for (C, H, N) (%) | Found (C, H, N) (%) | MS (EI) |
|---|---|---|---|---|---|---|---|---|---|---|---|
| XIII-11 | nBu | (Ph)₂CH | H | H | H | 2-(1-Tr-1H-tetrazol-5-yl)Ph | 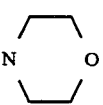 N—O | C₆₂H₅₈N₈O₃ | 77.31, 6.07, 11.63 | 77.49, 5.95, 11.57 | 963 (M⁺) |
| XIII-12 | nBu | (Ph)₂CH | H | H | H | 2-CN-Ph |  N—S | C₄₃H₄₃N₅O₂S | 74.43, 6.25, 10.09 | 74.56, 6.21, 9.97 | 694 (M⁺) |
| XIII-13 | nBu | (Ph)₂CH | H | H | H | 2-CN-Ph |  N—NH | C₄₃H₄₄N₆O₂ | 76.30, 6.55, 12.42 | 76.48, 6.50, 12.23 | 677 (M⁺) |

TABLE 17

| Compound No. | R¹ | R³ | R⁴ | R⁷ | R⁸ | R⁶ | R²' | Elementary analysis | Calcd. for (C, H, N) (%) | Found (C, H, N) (%) | MS(EI) |
|---|---|---|---|---|---|---|---|---|---|---|---|
| XIII-14 | nBu | (Ph)₂CH | H | H | H | 2-CN-Ph |  | C₄₂H₄₁N₅O₂ | 77.87, 6.38, 10.81 | 78.01, 6.29, 10.77 | 648(M⁺) |
| XIII-15 | nBu | (Ph)₂CH | H | H | H | 2-CN-Ph | 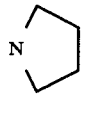 | C₄₃H₄₃N₅O₂ | 78.03, 6.55, 10.58 | 78.18, 6.48, 10.52 | 662(M⁺) |
| XIII-16 | nBu | (Ph)₂CH | H | H | H | 2-CN-Ph | 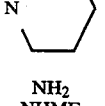 | C₄₄H₄₅N₅O₂ | 78.19, 6.71, 10.36 | 78.33, 6.64, 10.28 | 676(M⁺) |
| XIII-17 | nBu | (Ph)₂CH | H | H | H | 2-CN-Ph | NH₂ | C₃₉H₃₇N₅O₂ | 77.08, 6.14, 11.52 | 77.22, 6.05, 11.47 | 608(M⁺) |
| XIII-18 | nBu | (Ph)₂CH | H | H | H | 2-CN-Ph | NHME | C₄₀H₃₉N₅O₂ | 77.27, 6.32, 11.26 | 77.42, 6.28, 11.15 | 622(M⁺) |
| XIII-19 | nBu | (Ph)₂CH | H | H | H | 2-CN-Ph | N(Me)₂ | C₄₁H₄₁N₅O₂ | 77.45, 6.50, 11.02 | 77.61, 6.38, 10.95 | 636(M⁺) |
| XIII-20 | nBu | (Ph)₂CH | H | H | H | 2-CN-Ph | N(Et)₂ | C₄₃H₄₅N₅O₂ | 77.80, 6.83, 10.55 | 77.96, 6.74, 10.49 | 664(M⁺) |
| XIII-21 | nBu | (Ph)(c-Hex)CH | H | H | H | 2-CN-Ph | 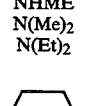 N—O | C₄₃H₄₉N₅O₃ | 75.52, 7.22, 10.24 | 75.71, 7.14, 10.15 | 684(M⁺) |
| XIII-22 | nHex | (Ph)₂CH | H | H | H | 2-CN-Ph | 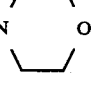 N—O | C₄₅H₄₇N₅O₃ | 76.57, 6.71, 9.92 | 76.71, 6.58, 9.86 | 706(M⁺) |

EXAMPLE 23

Process B, Step (j)

Synthesis of 4-[[(S)-2-n-butyl-1-[(4-carboxyphenyl)methyl]5-diphenylacetyl-4,5,6,7-tetrahydro-1H-imidazo[4,5-c]pyridin-6-yl]carbonyl]morpholine (I-29)

The compound (XIII-8) (0.0761 g, 0.00012 mol) was dissolved in a 1/1 mixture of THF and MeOH (1.52 ml), followed by addition of a 1N NaOH aqueous solution (0.38 ml), and the mixture was left as it was for 16.5 hours. The reaction mixture was concentrated, and a 1N HCl aqueous solution (0.43 ml) (pH 4) was added thereto to cause acid precipitation. The resulting oily material was dissolved in CHCl₃, washed with water, dried over Na₂SO₄, and concentrated to obtain the objective compound (I-29) (0.0735 g; yield: 98.8%) as a white foamy material.

¹H-NMR (CDCl₃+D₂O) δ: 0.84 (t, 3H, J=7.3 Hz), 1.27 (sext, 2H, J=7.3 Hz), 1.57 (quint, 2H, J=7.3 Hz), 2.55 (t, 2H, J=7.3 Hz), 2.70 (dd, 1H, J=6.0, 15.6 Hz), 2.86 (d, 1H, J=15.6 Hz), 3.30–3.65 (b, 8H), 4.24 (d, 1H, J=15.6 Hz), 5.06 (d, 1H, J=17.4 Hz), 5.10 (d, 1H, J=17.4 Hz), 5.12 (d, 1H, J=15.6 Hz), 5.43 (s, 1H), 5.97 (d, 1H, J=6.0 Hz), 7.12 (d, 2H, J=8.3 Hz), 7.17–7.33 (m, 10H), 8.09 (d, 2H, J=8.3 Hz).

IR (ν_max, KBr): 3460, 1715, 1646, 1453, 1412, 1270, 1230, 1115, 745, 700 cm⁻¹.

EXAMPLE 24

Process B, Step (k)

Synthesis of 4-[[(S)-1-[(4-amino-3-methylphenyl)methyl]-5-diphenytacetyl-4,5,6,7-tetrahydro-1H-imidazo[4,5-c]pyridin-6-yl]carbonyl]morpholine (I'-1)

The compound (XIII-3) (1.0079 g, 0.00174 mol) was dissolved in 10 ml of ethyl acetate, then tin chloride dihydrate (1.9632 g, 0.00870 mol) was added thereto. The mixture was stirred on an 80° C. oil bath in a stream of nitrogen for 30 minutes. The reaction mixture was cooled, neutralized with a 5% sodium carbonate aqueous solution, and concentrated. The residue was extracted with chloroform. The chloroform layer was washed with water, dried over anhydrous sodium sulfate, and concentrated to obtain a light-yellow foamy material. This substance was purified by silica gel column chromatography (chloroform/methanol=70/1) to obtain the objective compound (I'-1) (0.8781 g; yield: 91.9%) as a white foamy material.

$^1$H-NMR (CDCl$_3$) δ: 2.10 (s, 3H), 2.74 (dd, 1H, J=6.4, 15.6 Hz), 3.20 (d, 1H, J=15.6 Hz), 3.2–3.8 (b, 10H), 4.29 (d, 1H, J=14.8 Hz), 4.75 (d, 1H, J=14.8 Hz), 4.80 (d, 1H, J=15.0 Hz), 4.90 (d, 1H, J=15.0 Hz), 5.35 (s, 1H), 6.01 (d, 1H, J=6.4 Hz), 6.62 (d, 1H, J=8.3 HZ), 6.80 (d, 1H, J=8.3 Hz), 6.81 (s, 1H), 7.1–7.4 (m, 11H).

MS (EI): 550 (M+).

Elementary analysis Calcd. for C$_{33}$H$_{35}$N$_5$O$_3$ (%): C, 72.11; H, 6.42; N, 12.74. Found: C, 72.21; H, 6.35; N, 12.66.

EXAMPLE 25

Process B, Step (l)

Synthesis of 4-[[(S)-2-n-butyl-5-diphenylacetyl-1-[(2'-1H-tetrazol-5-yl)biphenyl-4-yl)methyl]-4,5,6,7-tetrahydro-1H-imidazo[4,5-c]pyridin-6-yl]carbonyl]morpholine (I-31)

Trimethyltin azide (0.0998 g, 0.000485 mol) was added to a solution of the compound (XIII-10) (0.1644 g, 0.000243 mol) in o-xylene (2.5 ml), and the mixture was stirred on a 120° C. oil bath in a nitrogen stream for 90 hours. The reaction mixture was cooled. The insoluble portion was filtered out, washed with hot toluene, and vacuum dried. The resulting light-yellow solid was dissolved in MeOH (1.8 ml), and a 1N HCl aqueous solution (0.9 ml) was added thereto, and the mixture was stirred at room temperature for 15 minutes. The reaction mixture was adjusted to pH 4 by adding a 1N NaOH aqueous solution and then concentrated, and the residue was extracted with CHCl$_3$. The chloroform layer was washed with water, dried over anhydrous sodium sulfate, and concentrated to obtain a light-yellow foamy material. This material was purified by silica gel column chromatography (chloroform/methanol=10/1) to obtain the objective compound (I-31) (0.1281 g; yield: 73.3%) as a white foamy material.

$^1$H-NMR (CDCl$_3$+D$_2$O) δ: 0.92 (t, 3H, J=7.3 Hz), 1.35 (sext, 2H, J=7.3 Hz), 1.52–1.73 (m, 2H), 1.38–2.75 (m, 4H), 3.20–3.67 (m, 8H), 3.76 (d, 1H, J=15.1 Hz), 4.54 (d, 1H, J=15.1 Hz), 4.92 (d, 1H, J=16.5 Hz), 5.05 (d, 1H, J=16.5 Hz), 5.14 (s, 1H), 5.81 (bs, 1H), 6.92–7.96 (m, 18H).

IR (ν$_{max}$, KBr): 3425, 1635, 1445, 1405, 1225, 1108, 748, 700 cm$^{-1}$.

MS (FAB): 721 (M+).

EXAMPLE 26

Process B, Step (m)

Synthesis of 4-[[(S)-5-diphenylacetyl-1-[(2'-(1H-tetrazol-5-yl)biphenyl-4-yl)methyl]-4,5,6,7-tetrahydro-1H-imidazo[4,5-c]pyridin-6-yl]carbonyl]morpholine (I-24)

A 12% HCl aqueous solution (5.5 ml) was added to a solution of the compound (XIII-5) (1.1103 g, 0.00122 mol) in THF (11 ml), and the mixture was stirred at room temperature for 4 hours. The reaction solution was neutralized by adding a 10% NaOH aqueous solution and concentrated. The residue was dissolved in a 1N NaOH aqueous solution and the insoluble portion was filtered out. The filtrate was adjusted to pH 4 by adding a 1N HCl aqueous solution and extracted with CHCl$_3$. The chloroform layer was washed with water, dried over anhydrous sodium sulfate, and concentrated to obtain a light-yellow foamy material. This material was purified by silica gel column chromatography (chloroform/methanol=10/1) to obtain the objective compound (I-24) (0.7413 g; yield: 91.1%) as a white foamy material.

$^1$H-NMR (D$_2$O+NaOD) δ: 2.71 (dd, 1H, J=7.2 Hz), 2.80 (d, 1H, J=15.1 Hz), 3.2–3.8 (b, 8H), 4.27 (d, 1H, J=15.1 Hz), 5.85 (b, 1H), 6.8–8.1 (m, 19H).

MASS (FAB): 665 (M+)

Elementary analysis Calcd. for C$_{39}$H$_{36}$N$_8$O$_3$ (%): C, 70.46; H, 5.46; N, 16.86. Found: C, 70.55; H, 5.40; N, 16.71.

EXAMPLE 27

Process B, Step (n)

Synthesis of 4-[[(S)-1-[[4-(2-carboxybenzamido)-3-methyl]phenyl]-methyl]-5-diphenylacetyl-4,5,6,7-tetrahydro-1H-imidazo[4,5-c]pyridin-6-yl]carbonyl]morpholine (1-23)

A solution of phthalic anhydride (0.3236 g, 0.00219 mol) in ethyl acetate (3.3 ml) was added to a solution of the compound (I'-1) (0.8007 g, 0.00146 mol) in ethyl acetate (12 ml) with stirring at room temperature, and the mixture was stirred for 23 hours. The reaction mixture was filtered, and the resulting white solid was washed with ethyl acetate and dried to obtain the objective compound (I-23) (0.8691 g; m.p. 191°–196° C.; yield: 85.5%).

$^1$H-NMR (D$_2$O+NaOD) δ: 2.24 (s, 3H), 2.30, 2.75 (each dd, 1H, J=5.6, 16.1 Hz), 2.95, 3.11 (each, d, 1H, J=16.1 Hz), 3.2–3.8 (b, 8H), 3.9–4.1 (m, 1H), 5.70 (b, 1H), 6.9–8.0 (m, 17H), 9.7 (b, 1H).

MASS (FAB): 698 (M+).

Elementary analysis Calcd. for C$_{41}$H$_{39}$N$_5$O$_6$ (%): C, 70.57; H, 5.63; N, 10.04. Found: C, 70.79; H, 5.48; N, 10.01.

The compounds shown in Tables 18 and 19 were synthesized in the similar way.

TABLE 18

| Compound No. | R¹ | R² | R³ | R⁴ | R | R⁷ | R⁸ | Elementary analysis | Calcd. for (C, H, N) (%) | Found (C, H, N) (%) | MS (FAB) |
|---|---|---|---|---|---|---|---|---|---|---|---|
| I-21 | H | CON(morpholino) | (Ph)₂CH | H | COOH | H | H | $C_{33}H_{32}N_4O_5$ | 70.20, 5.71, 9.92 | 70.39, 5.65, 9.88 | 565, M⁺ |
| I-22 | H | CON(morpholino) | (Ph)₂CH | H | COOH | Me | Me | $C_{35}H_{36}N_4O_5$ | 70.93, 6.12, 9.45 | 80.05, 6.08, 9.40 | 593, M⁺ |
| I-23 | H | CON(morpholino) | (Ph)₂CH | Me | NHCO(2-COOH-Ph) | H | H | $C_{41}H_{39}N_5O_6$ | 70.57, 5.63, 10.04 | 70.79, 5.48, 10.01 | 698, M⁺ |
| I-24 | H | CON(morpholino) | (Ph)₂CH | H | 2-(1H-tetrazol-5-yl)Ph | H | H | $C_{39}H_{36}N_8O_3$ | 70.46, 5.46, 16.86 | 70.55, 5.40, 16.71 | 665, M⁺ |
| I-25 | nPr | CON(morpholino) | (Ph)₂CH | H | 2-(1H-tetrazol-5-yl)Ph | H | H | $C_{42}H_{42}N_8O_3$ | 71.37, 5.99, 15.85 | 71.50, 5.92, 15.79 | 707, M⁺ |
| I-26 | iPr | CON(morpholino) | (Ph)₂CH | H | 2-(1H-tetrazol-5-yl)Ph | H | H | $C_{42}H_{42}N_8O_3$ | 71.37, 5.99, 15.85 | 71.46, 5.98, 15.81 | 707, M⁺ |
| I-27 | nBu | CH₂OH | (Ph)₂CH | H | COOH | H | H | $C_{33}H_{35}N_3O_4$ | 73.72, 6.56, 7.82 | 73.91, 6.49, 7.80 | 538, M⁺ |
| I-28 | nBu | COOH | (Ph)₂CH | H | COOH | H | H | $C_{33}H_{33}N_3O_5$ | 71.85, 6.03, 7.62 | 72.01, 5.98, 7.56 | 552, M⁺ |
| I-29 | nBu | CON(morpholino) | (Ph)₂CH | H | COOH | H | H | $C_{37}H_{40}N_4O_5$ | 71.59, 6.49, 9.03 | 71.66, 6.39, 8.99 | 621, M⁺ |
| I-30 | nBu | CON(morpholino) | (Ph)₂CH | Me | NHCO(2-COOH-Ph) | H | H | $C_{45}H_{47}N_5O_6$ | 71.69, 6.28, 9.29 | 71.77, 6.20, 9.25 | 754, M⁺ |
| I-31 | nBu | CON(morpholino) | (Ph)₂CH | H | 2-(1H-tetrazol-5-yl)Ph | H | H | $C_{43}H_{44}N_8O_3$ | 71.65, 6.15, 15.54 | 71.79, 6.10, 15.49 | 721, M⁺ |
| I-32 | nBu | CON(morpholino) | (Ph)₂CH | H | 2-(1H-tetrazol-5-yl)Ph | H | H | $C_{43}H_{44}N_8O_2S$ | 70.08, 6.02, 15.21 | 70.20, 5.98, 15.16 | 737, M⁺ |

TABLE 19

| Compound No. | R¹ | R² | R³ | R⁴ | R | R⁷ | R⁸ | Elementary analysis | Calcd. for (C, H, N) (%) | Found (C, H, N) (%) | MS (FAB) |
|---|---|---|---|---|---|---|---|---|---|---|---|
| I-33 | nBu | CON(piperazino-NH) | (Ph)₂CH | H | 2-(1H-tetrazol-5-yl)Ph | H | H | $C_{43}H_{45}N_9O_2$ | 71.74, 6.30, 17.51 | 71.89, 6.18, 17.49 | 720, M⁺ |

TABLE 19-continued

| Compound No. | R¹ | R² | R³ | R⁴ | R | R⁷ | R⁸ | Elementary analysis | Calcd. for (C, H, N) (%) | Found (C, H, N) (%) | MS (FAB) |
|---|---|---|---|---|---|---|---|---|---|---|---|
| I-34 | nBu | CON-(cyclobutyl) | (Ph)₂CH | H | 2-(1H-tetrazol-5-yl)Ph | H | H | $C_{42}H_{42}N_8O_2$ | 73.02, 6.13, 16.22 | 73.18, 6.09, 16.17 | 691, M⁺ |
| I-35 | nBu | CON-(cyclopentyl) | (Ph)₂CH | H | 2-(1H-tetrazol-5-yl)Ph | H | H | $C_{43}H_{44}N_8O_2$ | 73.27, 6.29, 15.90 | 73.45, 6.18, 15.88 | 705, M⁺ |
| I-36 | nBu | CON-(cyclohexyl) | (Ph)₂CH | H | 2-(1H-tetrazol-5-yl)Ph | H | H | $C_{44}H_{46}N_8O_2$ | 73.51, 6.45, 15.59 | 73.51, 6.45, 15.59 | 719, M⁺ |
| I-37 | nBu | CONH₂ | (Ph)₂CH | H | 2-(1H-tetrazol-5-yl)Ph | H | H | $C_{39}H_{38}N_8O_2$ | 71.98, 5.89, 17.22 | 72.10, 5.76, 17.19 | 651, M⁺ |
| I-38 | nBu | CONHMe | (Ph)₂CH | H | 2-(1H-tetrazol-5-yl)Ph | H | H | $C_{40}H_{40}N_8O_2$ | 72.27, 6.06, 16.86 | 72.49, 5.98, 16.79 | 665, M⁺ |
| I-39 | nBu | CON(Me)₂ | (Ph)₂CH | H | 2-(1H-tetrazol-5-yl)Ph | H | H | $C_{41}H_{42}N_8O_2$ | 72.54, 6.24, 16.51 | 72.70, 6.18, 16.47 | 679, M⁺ |
| I-40 | nBu | CON(Et)₂ | (Ph)₂CH | H | 2-(1H-tetrazol-5-yl)Ph | H | H | $C_{43}H_{46}N_8O_2$ | 73.06, 6.56, 15.85 | 73.21, 6.48, 15.80 | 707, M⁺ |
| I-41 | nBu | CON-(morpholino) | (Ph)(c-Hex)CH | H | 2-(1H-tetrazol-5-yl)Ph | H | H | $C_{43}H_{50}N_8O_3$ | 71.05, 6.93, 15,41 | 71.19, 6.90, 15.37 | 727, M⁺ |
| I-42 | nHex | CON-(morpholino) | (Ph)₂CH | H | 2-(1H-tetrazol-5-yl)Ph | H | H | $C_{45}H_{46}N_8O_3$ | 72.36, 6.21, 15.00 | 72.33, 6.39, 14.88 | 747, M⁺ |

There were also similarly synthesized the compounds shown in Table 20.

TABLE 20

| Compound No. | R¹ | R² | R³ | R⁴ | R⁷ | R⁸ | R¹⁰ | MS(EI) |
|---|---|---|---|---|---|---|---|---|
| I'-1 | H | CON-(morpholino) | (Ph)₂CH | Me | H | H | NH₂ | 550(M⁺) |
| I'-2 | nBu | CON-(morpholino) | (Ph)₂CH | Me | H | H | NH₂ | 606(M⁺) |

| Compound No. | Elementary analysis | Calcd. for (C, H, N) (%) | Found (C, H, N) (%) |
|---|---|---|---|
| I'-1 | $C_{33}H_{35}N_5O_3$ | 72.11, 6.42, 12.74 | 72.21, 6.35, 12.66 |
| I'-2 | $C_{37}H_{43}N_5O_3$ | 73.36, 7.15, 11.56 | 73.51, 7.02, 11.47 |

EXAMPLE 28

Process B, Step (o)

Synthesis of (S)-3-(2-n-butyl-1-triphenylmethyl-imidazol-5-yl)-2-(triphenylmethylamino)propan-1-ol (XXIV-3)

A 1.0M (nBu)₄NF/THF solution (2.6 ml, 0.00258 mol) was added to a solution of the compound (XIX-3) in dry THF (10 ml) with stirring under ice cooling, and the mixture was stirred under ice cooling for 30 minutes and further at room temperature for 3 hours. The reaction mixture was poured into water and extracted with EtOAc. The organic layer was washed with a saturated NaCl aqueous solution, dried over Na₂SO₄, and concentrated to obtain a white foamy material (1.0896 g, 100% up). This material was purified by silica gel column chromatography (hexane/acetone=5/1) to obtain the objective compound (XXIV-3) (0.7912 g; yield: 89.8%) as a white foamy material.

¹H-NMR (CD₂Cl₂) δ: 0.59 (t, 3H, J=7.3 Hz), 0.91 (sext, 2H, J=7.3 Hz), 1.11 (quint, 2H, J=7.3 Hz), 1.55

(bs, 1H, OH), 1.78–1.85 (m, 3H), 2.03 (b, 1H, NH), 2.23 (dd, 1H, J=3.2, 14.4 Hz), 2.80 (b, 1H, CH), 2.95 (dd, 1H, J=6.4, 11.5 Hz), 3.48 (dd, 1H, J=3.2, 11.5 Hz), 6.14 (s, 1H), 7.10–7.51 (m, 30H).

IR ($\nu_{max}$, KBr): 3452, 3105, 2900, 2975, 2905, 1510, 1456, 1410, 1160, 1036, 766, 744, 702, 640 cm$^{-1}$.

There were similarly synthesized the compounds shown in Table 21.

TABLE 21

| Compound No. | R$^1$ | Elementary Analysis | Calcd. for (C, H, N) (%) | Found (C, H, N) (%) | MS(EI) |
|---|---|---|---|---|---|
| XXIV-1 | nPr | C$_{47}$H$_{45}$N$_3$O | 84.52, 6.79, 6.29 | 84.71, 6.66, 6.10 | 668 |
| XXIV-2 | iPr | C$_{47}$H$_{45}$N$_3$O | 84.52, 6.79, 6.29 | 84.69, 6.71, 6.11 | 668 |
| XXIV-3 | nBu | C$_{48}$H$_{47}$N$_3$O | 84.54, 6.95, 6.16 | 84.70, 6.84, 6.08 | 682 |
| XXIV-4 | nHex | C$_{50}$H$_{51}$N$_3$O | 84.59, 7.24, 5.92 | 84.72, 7.15, 5.88 | 710 |

EXAMPLE 29

Process B, Step (p)

Synthesis of (S)-3-(2-n-butyl-1-triphenylmethyl-imidazol-5-yl)-2-(triphenylmethylamino) propanoic acid (XXV-3)

PDC (0.7845 g, 0.00208 mol) was added to a solution of the compound (XXIV-3) (0.4063 g, 0.000596 mol) in DMF (4.0 ml) and stirred at room temperature for 8 hours. The reaction mixture was poured into water and extracted with CH$_2$Cl$_2$. The organic layer was washed with water and then with a saturated NaCl aqueous solution, dried over Na$_2$SO$_4$, and concentrated to obtain a reddish brown oily product (0.5745 g, 100% up). This product was purified by silica gel column chromatography (hexane/acetone=2/1→1/2 and CHCl$_3$/MeOH=30/1) to obtain the objective compound (XXV-3) (0.1256 g; yield: 39.3%) as a light-yellow oily material.

$^1$H-NMR (CDCl$_3$) δ: 0.59 (t, 3H, J=7.3 Hz), 0.91 (sext, 2H, J=7.3 Hz), 1.16 (quint, 2H, J=7.3 Hz), 1.68–1.79 (m, 3H), 2.31 (dd, 1H, J=9.1, 15.3 Hz), 3.53 (d, 1H, J=9.1 Hz), 5.93 (s, 1H), 7.04–7.45 (m, 30H).

IR ($\nu_{max}$, KBr): 3025, 2980, 1715, 1608, 1510, 1460, 1410, 1390, 1370, 1190, 1158, 910, 730, 703 cm$^{-1}$.

The compounds shown in Table 22 were synthesized in the similar way.

TABLE 22

| Compound No. | R$^1$ | Elementary analysis | Calcd. for (C, H, N) (%) | Found (C, H, N) (%) | MS(FAB) |
|---|---|---|---|---|---|
| XXV-1 | nPr | C$_{47}$H$_{43}$N$_3$O$_2$ | 82.79, 6.36, 6.16 | 82.93, 6.27, 6.03 | 682(M$^+$) |
| XXV-2 | iPr | C$_{47}$H$_{43}$N$_3$O$_2$ | 82.79, 6.36, 6.16 | 82.88, 6.29, 6.08 | 682(M$^+$) |
| XXV-3 | nBu | C$_{48}$H$_{45}$N$_3$O$_2$ | 82.85, 6.52, 6.04 | 83.01, 6.44, 5.95 | 696(M$^+$) |
| XXV-4 | nHex | C$_{50}$H$_{49}$N$_3$O$_2$ | 82.95, 6.82, 5.80 | 83.11, 6.74, 5.68 | 724(M$^+$) |

EXAMPLE 30

Process B, Step (q)

Synthesis of (S)-2-amino-3-(2-n-butyl-1H-imidazol-5-yl)propanoic acid (XXV'-3) and (S)-2-n-butyl-4,5,6,7-tetrahydro-1H-imidazo[4,5-c]pyridine-6-carboxylic acid hydrochloride (XXVI-3)

A 1N HCl aqueous solution (3.3 ml) and a 37% HCHO solution (0.2 ml) were added to the compound (XXV-3) (0.3308 g, 0.000475 mol) and stirred at room temperature for 40 minutes and then in a 120° C. oil bath for 4 hours. After the reaction mixture was cooled, the insoluble portion was filtered out and washed with water. The aqueous layer was washed with Et$_2$O, then concentrated, and dried to obtain the objective compound (XXVI-3) (0.1401 g; yield: 99.5%) as a yellow viscous material.

$^1$H-NMR (D$_2$O+NaOD) δ: 0.95 (t, 3H, J=7.3 Hz), 1.40 (sext, 2H, J=7.3 Hz), 1.80 (quint, 2H, J=7.3 Hz), 3.03 (t, 2H, J=7.3 Hz), 3.0–3.4 (m, 2H), 3.8–4.3 (m, 2H).

MS (FAB): 223 (M-2HCl)

The compounds shown in Table 23 were similarly synthesized.

TABLE 23

| Compound No. | R$^1$ | MS (FAB) |
|---|---|---|
| XVIII-1 | nPr | 209 (M-2HCl) |
| XVIII-2 | iPr | 209 (M-2HCl) |
| XVIII-3 | nBu | 223 (M-2HCl) |
| XVIII-4 | nHex | 251 (M-2HCl) |

By using the compound (XXV-3) (0.3001 g, 0.000431 mol) and a 1N HCl aqueous solution (3.0 ml), the above reaction procedure was repeated without adding the 37% HCHO solution to obtain the compound (XXV'-3) (0.1225 g; yield: 100%) as a yellow viscous material.

$^1$H-NMR (D$_2$O+NaOD) δ: 0.96 (t, 3H, J=7.3Hz), 1.39 (sext, 2H, J=7.3Hz), 1.82 (quint, 2H, J=7.3Hz), 2.5–3.7 (m, 3H), 3.07 (t, 2H, J=7.3Hz), 6.85 (bs, 1H).

MASS (FAB): 211 (M-2HCl)

There were similarly synthesized the compounds shown in Table 24.

TABLE 24

| Compound No. | R$^1$ | MS (FAB) |
|---|---|---|
| XXV'-1 | nPr | 197 (M-2HCl) |
| XXV'-2 | iPr | 197 (M-2HCl) |
| XXV'-3 | nBu | 211 (M-2HCl) |
| XXV'-4 | nHex | 239 (M-2HCl) |

EXAMPLE 31

Process B, Step (r)

Synthesis of (S)-2-n-butyl-5-diphenylacetyl-4,5,6,7-tetrahydro-1H-imidazo[4,5-c]pyridine-6-carboxylic acid (XXVII-3)

Diphenylacetic acid (0.3114 g, 0.00147 mol), DCCI (0.3027 g, 0.00147 mol), and HBTA (0.1983 g, 0.00147 mol) were dissolved in dry THF (0.8 ml) and stirred at room temperature for 20 minutes. A solution of the compound (XXVI-3) (0.1358 g, 0.000458 mol) in dry THF (2.7 ml), and dry triethylamine (0.13 ml, 0.000963 mol) were added to this mixture, followed by stirring at room temperature for 16 hours. The insoluble portion was filtered out and washed with THF. The filtrate and washings were joined and concentrated to obtain a crude oily product (0.3065 g). This product was dissolved in a 1/1 mixture of THF and MeOH (6.0 ml) and, after addition of a 1N HCl aqueous solution (2.0 ml), left as it was for 8 hours. Further a 1/1 mixture of THF and MeOH (6.0 ml) and a 1N NaOH aqueous solution (4.0 ml) were added, and the mixture was left as it was for 8 hours. The reaction mixture was concentrated and the residue was purified by silica gel column chromatography (chloroform/methanol=10/1) to obtain the objective compound (XXVII-3) (0.0829 g; yield: 43.3%) as a white foamy material.

$^1$H-NMR (D$_2$O+NaOD) δ: 0.92 (t, 3H, J=7.2 Hz), 1.39 (sext, 2H, J=7.2 Hz), 1.82 (quint, 2H, J=7.2 Hz), 2.3–2.9 (m, 4H), 3.9–4.8 (m, 2H), 5.51 (s, 1H), 5.73 (bs, 1H), 7.1–7.7 (m, 10H).

MASS (FAB): 417 (M+)

Elementary analysis Calcd. for C$_{25}$H$_{27}$N$_3$O$_3$ (%): C, 71.92; H, 6.52; N, 10.06. Found: C, 72.08; H, 6.47; N, 9.99.

The compounds shown in Table 25 were similarly synthesized.

the angiotensin II receptor type 1 (AT$_1$) and at 37° C. for one hour for the type 2 (AT$_2$)), the reaction mixture was subjected to suction filtration (using GF/C filter paper for AT$_1$ and GF/B filter paper for AT$_2$). The filter paper (tracer-receptor complex) after suction filtration was measured by a γ-well counter (ARC-500, Aloka). The non-specific binding was determined by the similar operation by using a large excess of displacer. The specific binding at the predetermined concentration of the test drug was calculated by deducting the non-specific binding from the total binding.

The ratio (%) at which the test drugs inhibit binding between radioactive ligand and receptor was determined for both AT$_1$ and AT$_2$ by using the test drugs of the predetermined concentration and a control drug.

The compound of the present invention competes with both of the angiotensin II receptors AT$_1$ and AT$_2$, but it is noted that the compound of the formula (I) wherein R$_1$ is H competes specifically with AT$_2$ and that of the formula (I) wherein R$_1$ is other than H competes specifically with AT$_1$.

In U.S. Pat. No. 5,091,390, it is stated that the compounds claimed therein, including some reference com-

TABLE 25

| Compound No. | R$^1$ | R$^3$ | Elementary analysis | Calcd. for (C, H, N) (%) | | | Found (C, H, N) (%) | | | MS(FAB) |
|---|---|---|---|---|---|---|---|---|---|---|
| XXVII-1 | nPr | (Ph)$_2$CH | C$_{24}$H$_{25}$N$_3$O$_3$ | 71.44, | 6.25, | 10.41 | 71.61, | 6.17, | 10.35 | 403(M+) |
| XXVII-2 | iPr | (Ph)$_2$CH | C$_{24}$H$_{25}$N$_3$O$_3$ | 71.44, | 6.25, | 10.41 | 71.59, | 6.19, | 10.37 | 403(M+) |
| XXVII-3 | nBu | (Ph)$_2$CH | C$_{25}$H$_{27}$N$_3$O$_3$ | 71.92, | 6.52, | 10.06 | 80.07, | 6.48, | 9.98 | 417(M+) |
| XXVII-4 | nHex | (Ph)$_2$CH | C$_{27}$H$_{31}$N$_3$O$_3$ | 72.78, | 7.01, | 9.43 | 72.91, | 6.94, | 9.35 | 446(M+) |
| XXVII-5 | nBu | (Ph)(c-Hex)CH | C$_{25}$H$_{33}$N$_3$O$_3$ | 70.89, | 7.85, | 9.92 | 71.01 | 7.78 | 9.85 | 424(M+) |

EXAMPLE 32

Process B, Step (s)

Synthesis of (S)-2-n-butyl-1-[(4-methoxycarbonylphenyl)methyl]-5-diphenylacetyl-4,5,6,7-tetrahydro-1H-imidazo[4,5-c]pyridine-6-carboxylic acid (XIV-8)

Methyl 4-(bromomethyl)benzoate (0.0521 g, 0.000227 mol) and K$_2$CO$_3$ (0.0314 g, 0.000227 mol) were added to a solution of the compound (XXVII-3) (0.0791 g, 0.000189 mol) in dry DMF (1.6 ml), and the mixture was stirred vigorously at room temperature for 20 hours. The reaction mixture was poured into water, extracted with EtOAc, washed with water, dried over anhydrous sodium sulfate, and concentrated to obtain a light-yellow oily material. This material was purified by silica gel column chromatography (hexane/acetone=1/2) to obtain the objective compound (XIV-8) (0.0331g; m.p. 176°–180° C.), its 3-position isomer (0.0382 g) and a mixture of them (0.0018 g; yield: 68.2%) as colorless crystals.

MASS (FAB): 566 (M+)

Elementary analysis Calcd. for C$_{34}$H$_{35}$N$_3$O$_5$ (%): C, 72.19; H, 6.24; N, 7.43. Found: C, 72.30; H, 6.21; N, 7.39.

EXAMPLE 33

Receptor binding test

Determination of total binding in the presence of each drug to be tested was made in the following way. A test drug of a predetermined concentration (0.025 ml; dissolved in dimethyl sulfoxide, then diluted two-fold with a buffer attached to the Drug Discovery System and used for assay), a tracer (0.025 ml), and a receptor (0.2 ml) were added to make a total volume of 0.25 ml. After incubation (at room temperature for 3 hours for pounds described below, compete selectively with AT$_2$ regardless of R$^1$, but the present inventors found that the compound of the present invention and the reference compounds compete specifically with one of AT$_1$ and AT$_2$ receptors according to the difference of R$^1$, and that the activity of the compound of the present invention far excels that of the reference compounds.

TABLE 26

| | Binding inhibition ratio (%) of the test compounds at 1 μM | |
|---|---|---|
| Test compound | AT$_1$* | AT$_2$** |
| Compound I-1 | 0 | 100 |
| Compound I-2 | 0 | 100 |
| Compound I-7 | 0 | 100 |
| Compound I-12 | 100 | 0 |
| Compound I-17 | 100 | 0 |
| Compound I-19 | 100 | 0 |
| Compound I-21 | 0 | 100 |
| Compound I-23 | 0 | 100 |
| Compound I-24 | 0 | 100 |
| Compound I-30 | 100 | 0 |
| Compound I-31 | 100 | 0 |
| Compound I-32 | 100 | 0 |
| Compound I-40 | 100 | 0 |
| Reference compound PD123177 | 0 | 65 |
| Reference compound DuP753 | 70 | 0 |
| Reference compound 1 | 0 | 71 |
| Reference compound 2 | 0 | 72 |
| Reference compound 26 | 78 | 0 |
| Reference compound 27 | 0 | 76 |
| Reference compound 50 | 75 | 0 |

*Receptor: suprarenal gland of rabbit Tracer: $^3$H-angiotensin II (displacer: DuP753)
**Receptor: bovine cerebellar cortex Tracer: $^{125}$I-Tyr$^4$-angiotensin II (displacer: angiotensin II (human))

PD123177 and DuP753 are disclosed in Bioorganic & Medical Chemistry Letters, 1(12), 711–716, 1991.

PD123177

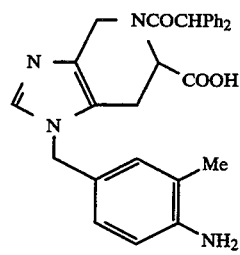

DuP753

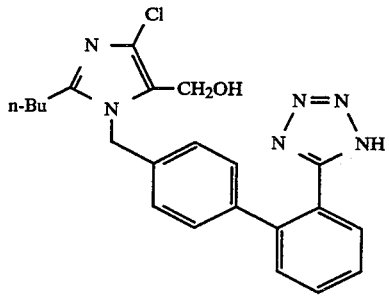

Comparative substances 1, 2, 26, 27 and 50 are the compounds disclosed in U.S. Pat. No. 5,091,390:

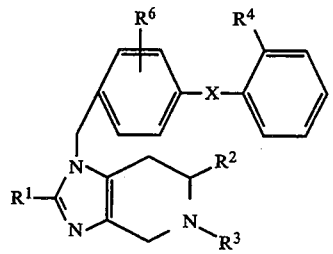

| Reference compound | R¹ | R² | R³ | X | R⁴ | R⁶ |
|---|---|---|---|---|---|---|
| 1 | H | COOH | COCH(Ph)₂ | NHCO | COOH | 3-CH₃ |
| 2 | H | COOCH₃ | COCH(Ph)₂ | NHCO | COOH | 3-CH₃ |
| 26 | C₃H₇ | COOH | COCH(Ph)₂ | single bond | tetrazolyl | 3-CH₃ |
| 27 | H | COOH | COCH(Ph)₂ | single bond | tetrazolyl | H |
| 50 | C₃H₇ | COOH | COCH(Ph)₂ | single bond | tetrazolyl | H |

What is claimed is:
1. A compound of the formula (I):

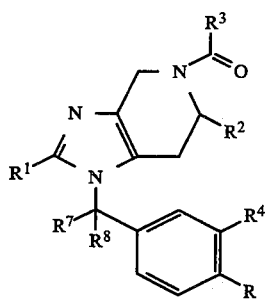

(I)

or a pharmaceutically acceptable salt thereof; wherein R¹ represents
   hydrogen atom,
   halogen atom,
   $C_1$-$C_6$ alkyl,
   $C_3$-$C_6$ alkenyl,
   $C_3$-$C_6$ alkynyl,
   $R^{20}(CH_2)_n$— wherein $R^{20}$ represents $C_3$-$C_8$ cycloalkyl, naphthyl, phenyl, or phenyl substituted with one to five of $C_1$-$C_4$ alkyl, halogen atom, trifluoromethyl, hydroxy, $C_1$-$C_4$ alkoxy, $C_1$-$C_3$ acyloxy, amino, N-mono-$C_1$-$C_4$ alkylamino, N-di-$C_1$-$C_4$ alkylamino, $C_1$-$C_4$ thioalkyl, $C_1$-$C_3$ alkylsulfonyl, nitro, and —NHCOR²¹ wherein R²¹ represents $C_1$-$C_3$ alkyl, phenyl, $C_1$-$C_3$ alkylphenyl, aminophenyl, or $C_1$-$C_4$ alkylaminophenyl, and n is an integer of 1 to 6,
   $R^{20}$—C(O)— wherein $R^{20}$ is as defined above, or
   $R^{20}$—CH(OH)— wherein $R^{20}$ is as defined above;
R² represents carbamoyl, mono- or di-$C_1$-$C_6$ alkylcarbamoyl, or 4- to 6-membered saturated N, S or O-containing heterocyclic carbamoyl;
R represents amino, carboxy, (1H-tetrazol-5-yl)phenyl, carboxyphenyl, carboxybenzamido, (1H-tetrazol-5-yl)benzamido, carboxyphenylcarbamoyl, or (1H-tetrazol-5-yl)-phenylcarbamoyl;
represents —CH₂(phenyl), —CH(phenyl)₂, —CH(phenyl)CH₃, —CH(phenyl)(cyclohexyl), —CH₂CH₂(phenyl), —CH₂($C_1$-$C_6$ alkoxyphenyl), or —CH₂(hydroxyphenyl); and
R⁴, R⁷, and R⁸ each represent independently hydrogen atom or $C_1$-$C_6$ alkyl.

2. A compound or a pharmaceutically acceptable salt thereof according to claim 1, wherein R¹ is hydrogen atom or $C_1$-$C_6$ alkyl group; R² is —CONH₂, —CONHCH₃, —CON(CH₃)₂, —CONH(C₂H₅), —CON(C₂H₅)₂,

—CON⟨▱⟩, —CON⟨▱⟩, —CON⟨▱⟩,

—CON⟨O⟩, —CON⟨S⟩, or —CON⟨NH⟩;

R is amino, carboxy, 2-(1H-tetrazol-5-yl)phenyl, 2-carboxyphenyl, 2-carboxybenzamido, 2-(1H-tetrazol-5-yl)benzamido, 2-carboxyphenylcarbamoyl, or 2-(1H-tetrazol-5-yl)phenylcarbamoyl; R³ is —CH(phenyl)₂, —CH₂(phenyl), —CH(phenyl)CH₃, —CH(phenyl)(cyclohexyl), —CH₂CH₂(phenyl), —CH₂(p-methoxyphenyl), or —CH$_2$(p-hydroxyphenyl); and R$^4$, R$^7$, and R$^8$ each are independently hydrogen atom or C$_1$-C$_2$ alkyl.

3. A compound of the formula (XIII):

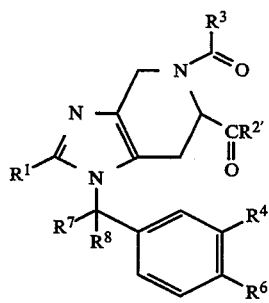

(XIII)

or a salt thereof; wherein
R$^1$ represents
hydrogen atom,
halogen atom,
C$_1$-C$_6$ alkyl,
C$_3$-C$_6$ alkenyl,
C$_3$-C$_6$ alkynyl,
R$^{20}$(CH$_2$)$_n$— wherein R$^{20}$ represents C$_3$-C$_8$ cycloalkyl, naphthyl, phenyl, or phenyl substituted with one to five of C$_1$-C$_4$ alkyl, halogen atom, trifluoromethyl, hydroxy, C$_1$-C$_4$ alkoxy, C$_1$-C$_3$ acyloxy, amino, N-mono-C$_1$-C$_4$ alkylamino, N-di-C$_1$-C$_4$ alkylamino, C$_1$-C$_4$ thioalkyl, C$_1$-C$_3$ alkylsulfonyl, nitro, and —NHCOR$^{21}$ wherein R$^{21}$ represents C$_1$-C$_3$ alkyl, phenyl, C$_1$-C$_3$ alkylphenyl, aminophenyl, or C$_1$-C$_4$ alkylaminophenyl, and n is an integer of 1 to 6,
R$^{20}$—C(O)— wherein R$^{20}$ is as defined above, or
R$^{20}$—CH(OH)— wherein R$^{20}$ is as defined above;
R$^{2'}$ represents amino, mono or di-C$_1$-C$_6$ alkylamino, or 4- to 6-membered saturated N, S or O-containing heterocyclic amino;
R$^3$ represents —CH$_2$(phenyl), —CH(phenyl)$_2$, —CH(phenyl) CH$_3$, —CH(phenyl)(cyclohexyl), —CH$_2$CH$_2$(phenyl), —CH$_2$(C$_1$-C$_6$ alkoxyphenyl), or —CH$_2$(hydroxyphenyl);
R$^4$, R$^7$, and R$^8$ each represent independently hydrogen atom or C$_1$-C$_6$ alkyl; and
R$^6$ represents nitro, (1-triphenylmethyl-1H-tetrazol-5-yl)phenyl, C$_1$-C$_3$ alkoxycarbonyl, cyano, or 2-cyanophenyl.

4. A compound or a salt thereof according to claim 3, wherein R$^1$ is hydrogen atom or C$_1$-C$_6$ alkyl; R$^2$ is —NH$_2$, —NHCH$_3$, —N(CH$_3$)$_2$, —NH(C$_2$H$_5$), N(C$_2$H$_5$)$_2$,

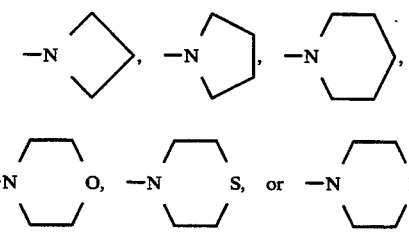

R$^3$ is —CH(phenyl)$_2$, —CH(phenyl)(cyclohexyl); R$^4$, R$^7$, and R$^8$ each are independently hydrogen atom or C$_1$-C$_2$ alkyl; and R$^6$ is nitro, 2-(1-triphenylmethyl-1H-tetrazol-5-yl)phenyl, methoxycarbonyl, cyano, or 2-cyanophenyl.

5. An angiotensin II antagonist comprising the compound or the pharmaceutically acceptable salt thereof as defined in claim 1.

6. An angiotensin II AT$_1$ receptor antagonist comprising a compound of the formula (I):

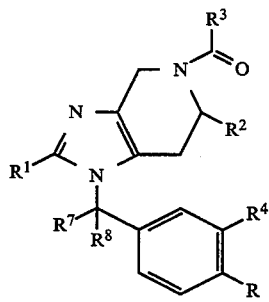

(I)

or a pharmaceutically acceptable salt thereof; wherein
R$^1$ represents
halogen atom,
C$_1$-C$_6$ alkyl,
C$_3$-C$_6$ alkenyl,
C$_3$-C$_6$ alkynyl,
R$^{20}$ (CH$_2$)$_n$— wherein R$^{20}$ represents C$_3$-C$_8$ cycloalkyl, naphthyl, phenyl, or phenyl substituted with one to five of C$_1$-C$_4$ alkyl, halogen atom, trifluoromethyl, hydroxy, C$_1$-C$_4$ alkoxy, C$_1$-C$_3$ acyloxy, amino, N-mono-C$_1$-C$_4$ alkylamino, N-di-C$_1$-C$_4$ alkylamino, C$_1$-C$_4$ thioalkyl, C$_1$-C$_3$ alkylsulfonyl, nitro, and —NHCOR$^{21}$ wherein R$^{21}$ represents C$_1$-C$_3$ alkyl, phenyl, C$_1$-C$_3$ alkylphenyl, aminophenyl, or C$_1$-C$_4$ alkylaminophenyl, and n is an integer of 1 to 6,
R$^{20}$—C(O)— wherein R$^{20}$ is as defined above, or
R$^{20}$—CH(OH)— wherein R$^{20}$ is as defined above;
R$^2$ represents carbamoyl, mono- or di-C$_1$-C$_6$ alkylcarbamoyl, or 4- to 6-membered saturated N, S, or O-containing heterocyclic carbamoyl;
R represents amino, carboxy, (1H-tetrazol-5-yl)phenyl, carboxyphenyl, carboxybenzamido, (1H-tetrazol-5-yl)benzamido, carboxyphenylcarbamoyl, or (1H-tetrazol-5-yl)-phenylcarbamoyl;
R$^3$ represents —CH$_2$(phenyl), —CH(phenyl)$_2$, —CH(phenyl) CH$_3$, —CH(phenyl)(cyclohexyl), —CH$_2$CH$_2$(phenyl), —CH$_2$(C$_1$-C$_6$ alkoxyphenyl), or —CH$_2$(hydroxyphenyl); and
R$^4$R$^7$, and R$^8$ each represent independently hydrogen atom or C$_1$-C$_6$ alkyl.

7. An angiotensin II AT$_2$ receptor antagonist comprising a compound of the formula (I):

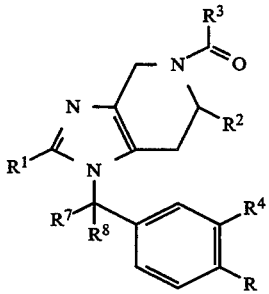

(I)

or a pharmaceutically acceptable salt thereof; wherein
R$^1$ represents hydrogen atom, $R^2$ represents carbamoyl, mono- or di-$C_1$-$C_6$ alkylcarbamoyl, or 4- to 6-membered saturated N, S, or O-containing heterocyclic carbamoyl;

R represents amino, carboxy, (1H-tetrazol-5-yl)phenyl, carboxyphenyl, carboxybenzamido, (1H-tetrazol-5-yl)benzamido, carboxyphenylcarbamoyl, or (1H-tetrazol-5-yl)-phenylcarbamoyl;

$R^3$ represents —$CH_2$(phenyl), —CH(phenyl)$_2$, —CH(phenyl)$CH_3$, —CH(phenyl)(cyclohexyl), —$CH_2CH_2$(phenyl), —$CH_2$($C_1$-$C_6$ alkoxyphenyl), or —$CH_2$(hydroxyphenyl); and $R^4$, $R^7$, and $R^8$, each represent independently hydrogen atom or $C_1$-$C_6$ alkyl.

* * * * *

UNITED STATES PATENT AND TRADEMARK OFFICE
CERTIFICATE OF CORRECTION

PATENT NO.   : 5,401,736
DATED        : March 28, 1995
INVENTOR(S) : ENARI et al

It is certified that error appears in the above-identified patent and that said letters patent is hereby corrected as shown below:

Column 48, line 21, before "represents" insert --$R^3$--. Column 50, line 49, change "$R^4R^7$" to --$R^4$, $R^7$--. Column 52, line 6, change "$R^8$, each" to --$R^8$ each--.

Signed and Sealed this

Twenty-fifth Day of July, 1995

Attest:

BRUCE LEHMAN

*Attesting Officer*              *Commissioner of Patents and Trademarks*

UNITED STATES PATENT AND TRADEMARK OFFICE
CERTIFICATE OF CORRECTION

PATENT NO. : 5,401,736
DATED : March 28, 1995
INVENTOR(S) : Enari et al

It is certified that error appears in the above-indentified patent and that said Letters Patent is hereby corrected as shown below:

In the title, item [54] and column 1, line 2, add —DERIVATIVES— after "AMIDE".

Columns 3-4, Scheme I, center structure, delete "(VI)" and replace by --(VII)--.

Column 6 line 50, delete "above" and replace by --"above.--".

Column 11 lines 6-7, delete "Tr (triphenylmethyl) chloride and triethylamine" and replace by --triethylamine and Tr (triphenylmethyl) chloride--.

Column 12 line 12, delete "(XIV)" and replace by --(XIII)--; line 34, delete "1H-tetrazol-5-yl) and replace by --(1H-tetrazol-5-yl)--.

UNITED STATES PATENT AND TRADEMARK OFFICE
CERTIFICATE OF CORRECTION

PATENT NO. : 5,401,736

DATED : March 28, 1995

INVENTOR(S) : Enari et al

It is certified that error appears in the above-indentified patent and that said Letters Patent is hereby corrected as shown below:

Column 13 line 29, delete "(III')" and replace by --(VIII')--.

Column 15 line 9, delete "$R^3$" and replace by --$R^{3'}$-- and line 62, delete "$R^{15}$" and replace by --$R^{15'}$--.

Column 17 line 48, delete "et." and replace by --etc.--.

Column 18 line 14, delete "5.34" and replace by --5.43--.

Column 19 line 3, delete "(S)"; line 4, insert --(S)-- before "-1-(3-methyl-4-nitrophenyl)".

UNITED STATES PATENT AND TRADEMARK OFFICE
CERTIFICATE OF CORRECTION

PATENT NO. : 5,401,736  
DATED : March 28, 1995  
INVENTOR(S) : Enari et al

Page 3 of 7

It is certified that error appears in the above-indentified patent and that said Letters Patent is hereby corrected as shown below:

Column 20 line 30, delete "top" and replace by --m.p.--.

Column 21 TABLE 4, row of "III-8" and column of "$R^2$", delete "NH2" and replace by --$NH_2$--; TABLE 4, row of "III-9" and column of "$R^2$", delete "NHME" and replace by --NHMe--; TABLE 4, row of "III-13" and column of "$R^1$", delete "nhex" and replace by --nHex--.

Column 22 line 18, delete "chloroform methanol" and replace by --chloroform/methanol--; TABLE 5, row of "II-13" and column of "$R^1$", delete "nhex" and replace by --nHex--.

Column 23 TABLE 6, row of "I-2" and column of "$R^2$", delete "NM 2" and replace by --$NMe_2$--.

UNITED STATES PATENT AND TRADEMARK OFFICE
CERTIFICATE OF CORRECTION

PATENT NO. : 5,401,736
DATED : March 28, 1995
INVENTOR(S) : Enari et al

It is certified that error appears in the above-indentified patent and that said Letters Patent is hereby corrected as shown below:

Column 23 TABLE 6, row of "I-9" and column "$R^2$", delete "NHME" and replace by --NHMe--; TABLE 6, row of "I-13" and column "MS(EI)", delete "721 (m-18)" and replace by --721 (M-18)-- and TABLE 7, row of "I-7" and column of "Found (C, H, N), delete "70.4S, 5.71, 10.06" and replace by --70.45, 5.71, 10.06--.

Column 24 line 16, delete "[[" and replace by --[--.

Column 25 TABLE 8, row of "I-16" and column of "MS(EI)", delete "622 (M+) and replace by --622($M^+$)--; TABLE 8, row of "I-18" and column of "MS (EI)", delete "678 (M+) and replace by --678 ($M^+$)--.

UNITED STATES PATENT AND TRADEMARK OFFICE
CERTIFICATE OF CORRECTION

PATENT NO. : 5,401,736
DATED : March 28, 1995
INVENTOR(S) : Enari et al

It is certified that error appears in the above-indentified patent and that said Letters Patent is hereby corrected as shown below:

Column 25 TABLE 8 row of "I-19" and column of "$R^3$", delete "Cfl (Ph) 2" and replace by --$CH(Ph)_2$--; TABLE 8, row of "I-19" and column of "R", delete "2-(IH-tetrazol-5-yl) phenyl" and replace by --2-(1H-tetrazol-5-yl) phenyl--; TABLE 8, row of "I-19" and column of "MS (EI)", delete "692 (M+)" and replace by --692 ($M^+$)--; TABLE 8, row of "I-20" and column of "MS (EI)", delete "720 (M+)" and replace by --720 ($M^+$)--; TABLE 9, row of "I-18" and column of "Found (C, H, N)", delete "2.49, 6.30, 16.48" and replace by --72.49, 6.30, 16.48-- and TABLE 9, row of "I-19" and column of "Calcd. for (C, H, N)", delete "72.81, 6.40, 16.1" and replace by --72.81, 6.40, 16.17--.

Column 27, TABLE 11, row of "XVII-2" and column of "$R^1$" delete "nhex" and replace by --iPr--; row of "XVII-4" and column of "$R^1$", delete "nhex" and replace by --nHex--.

UNITED STATES PATENT AND TRADEMARK OFFICE
CERTIFICATE OF CORRECTION

PATENT NO. : 5,401,736
DATED : March 28, 1995
INVENTOR(S) : Enari et al

It is certified that error appears in the above-indentified patent and that said Letters Patent is hereby corrected as shown below:

Columns 35-36, TABLE 17, row of "XIII-18" and column of "$R^2$", delete "NHME" and replace by --NHMe--.

Column 35, line 66, delete "(pH 4)" and line 67, insert --(pH 4.0)-- after "precipitation".

Column 37 line 7, delete "diphenytacetyl" and replace by --diphenylacetyl-- and line 29, delete "8.3 HZ" and replace by --8.3 Hz--.

Columns 39-40, TABLE 18, row of "I-32" and column of "$R^2$", delete

 "CON⟨ ⟩O" and replace by --CON⟨ ⟩S--.

UNITED STATES PATENT AND TRADEMARK OFFICE
CERTIFICATE OF CORRECTION

PATENT NO. : 5,401,736
DATED : March 28, 1995
INVENTOR(S) : Enari et al

It is certified that error appears in the above-indentified patent and that said Letters Patent is hereby corrected as shown below:

Column 43 line 21, delete "triphenylmethyl-imidazol" and replace by --triphenylmethylimidazol--.

Column 44 TABLE 23, delete "XVIII" and replace by --XXVI--; line 63, delete "0.8 ml" and replace by --8.0 ml--.

Column 49 line 41, delete "phenyl) CH$_3$" and replace by --phenyl) CH$_3$--.

Column 50 line 46, delete "phenyl) CH$_3$" and replace by --phenyl) CH$_3$--.

Signed and Sealed this

Fifth Day of December, 1995

BRUCE LEHMAN

Attest:

Attesting Officer

Commissioner of Patents and Trademarks